(12) United States Patent
Verdin et al.

(10) Patent No.: US 7,488,587 B2
(45) Date of Patent: Feb. 10, 2009

(54) HISTONE DEACETYLASE AND METHODS OF USE THEREOF

(75) Inventors: Eric Verdin, San Francisco, CA (US); Wolfgang Fischle, Charlottesville, VA (US); Franck O. Dequiedt, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 988 days.

(21) Appl. No.: 10/175,559

(22) Filed: Jun. 17, 2002

(65) Prior Publication Data

US 2003/0143712 A1 Jul. 31, 2003

Related U.S. Application Data

(60) Provisional application No. 60/299,228, filed on Jun. 19, 2001.

(51) Int. Cl.
*C07H 21/00* (2006.01)
*C07H 21/02* (2006.01)
(52) U.S. Cl. .................................. 435/69.1; 536/23.1
(58) Field of Classification Search ................ 536/23.1; 236/23.1; 435/69.1
See application file for complete search history.

(56) References Cited

U.S. PATENT DOCUMENTS

2003/0129724 A1* 7/2003 Grozinger et al. ........... 435/226

FOREIGN PATENT DOCUMENTS

| WO | WO 01/42437 A | 6/2001 |
|---|---|---|
| WO | WO 03/006652 A2 | 1/2003 |

OTHER PUBLICATIONS

GenEmbl database for nucleotide sequences (Accession No. AF239243, Apr. 12, 2000).*
GenEmbl database for nucleotide sequences (Accession No. AL117455, Feb. 18, 2000).*
Kao et al. (Gene. Dev. 2000; 14: 55-66).*
Database on Genbank, Li et al. "A novel class II HDAC is associated with the transcriptional homeodomain repressor CCAAT displacement protein," Jun. 1, 2001, Accession No. Q9NYK9.
Database on Genbank, Shimkets et al. Human ORFX ORF2609 polynucleotide sequence SEQ ID No. 5217. Oct. 5, 2000, Accession No. AAC77054.
Database on Genbank, Li et al. "A novel class II HDAC is associated with the transcriptional homeodomain repressor CCAAT displacement protein," Apr. 12, 2000, Accession No. AF239243.
Bertos et al. Class II histone deacetylase: Structure, function, and regulation. *Biochem. Cell. Biol.*, May 14, 2001, vol. 79, No. 3 pp. 243-252.
Miska et al. (1999) *EMBO J.* 18:5099-5107.
Lemercier et al. (2000) *J. Biol. Chem.* 275:15594-15599.
Grozinger et al. (2000) *Proc. Natl. Acad. Sci. USA* 97:7835-7840.
Huynh et al. (2000) *Genes and Development* 14:1810-1823.
Huang et al. (2000) *Genes Dev.* 14:45-54.
Kao et al. (2000) *Genes Dev.* 14:55-66.
Kao et al., "Isolation of a novel histone deacetylase reveal that class I and class II deacetylases promote SMRT-mediated repression", (2000), Genes & Development, vol. 14, pp. 55-66.
Fischle et al., (1999), "A New Family of Human Histone Deacetylases Related to Saccharomyces cerevisiae HDA1p" The Journal of Biological Chemistry, 274: 11713-11720.
Fischle et al., (2001) "Human HDAC7 Histone Deacetylase Activity Is Associated with HDAC3 in Vivo" The Journal of Biological Chemistry, 276: 35826-35835.
Fischle et al., (2001) "The Emerging Role of Class II Histone Deacetylases" Biochemistry and Cell Biology, 79: 337-348.
Weidle U.H. et al. "Inhibition of Histone Deacetylases: A New Strategy to Target Epigenetic Modifications for Anticancer Treatment" Anticancer Research, Helenic Anticancer Institute, Athens, GR. vol. 20, May 2000, pp. 1471-1485.
Sawa H. et al., "Histone deacetylase inhibitors such as sodium butyrate and trichostatin A induce apoptosis through an increase of the bcl-2-related protein Bad" Brain Tumor Pathology. 2001, vol. 18, No. 2, 2001, pp. 109-114.
Penn L.Z., "Apoptosis Modulators as Cancer Therapeutics" Current Opinion in Investigational Drugs, Current Drugs, London, GB, vol. 2, No. 5, May 2001, pp. 684-692.
Database Genbank, Aug. 28, 1998, "Homo sapiens 12q13.1 PAC RPCI5-1057120 (Rosewell Park Cancer Institute Human PAC Library) complete sequence" retrieved from NCBI, Database accession No. AC004466.

* cited by examiner

*Primary Examiner*—Brandon J Fetterolf
(74) *Attorney, Agent, or Firm*—Paula A. Borden; Bozicevic, Field & Francis LLP; Michael B. Rubio

(57) ABSTRACT

The present invention provides nucleic acid molecules that encode histone deacetylase, as well as recombinant vectors and host cells that include the subject nucleic acid molecules. Also provided are histone deacetylase polypeptide compositions. The histone deaceylase nucleic acid molecules are useful in a variety of diagnostic and therapeutic applications, which are also provided.

12 Claims, 10 Drawing Sheets

FIG. 1i

```
CAGCCCATGG ACCTGCGGGT GGGCCAGCGG CCCCCAGTGG AGCCCCCACC AGAGCCCACA
TTGCTGGCCC TGCAGCGTCC CCAGCGCCTG CACCACCACC TCTTCCTAGC AGGCCTGCAG
CAGCAGCGCT CGGTGGAGCC CATGAGGCTC TCCATGGACA CGCCGATGCC CGAGTTGCAG
GTGGGACCCC AGGAACAAGA GCTGCGGCAG CTTCTCCACA AGGACAAGAG CAAGCGAAGT
GCTGTAGCCA GCAGCGTGGT CAAGCAGAAG CTAGCGGAGG TGATTCTGAA AAAACAGCAG
GCGGCCCTAG AAAGAACAGT CCATCCCAAC AGCCCCGGCA TTCCCTACAG AACCCTGGAG
CCCCTGGAGA CGGAAGGAGC CACCCGCTCC ATGCTCAGCA GCTTTTTGCC TCCTGTTCCC
AGCCTGCCCA GTGACCCCCC AGAGCACTTC CCTCTGCGCA AGACAGTCTC TGAGCCCAAC
CTGAAGCTGC GCTATAAGCC CAAGAAGTCC CTGGAGCGGA GGAAGAATCC ACTGCTCCGA
AAGGAGAGTG CGCCCCCCAG CCTCCGGCGG CGGCCCGCAG AGACCCTCGG AGACTCCTCC
CCAAGTAGTA GCAGCACGCC CGCATCAGGG TGCAGCTCCC CCAATGACAG CGAGCACGGC
CCCAATCCCA TCCTGGGCTC GGAGGCTGAC AGTGACCGCA GGACCCATCC GACTCTGGGC
CCTCGGGGGC CAATCCTGGG GAGCCCCCAC ACTCCCCTCT TCCTGCCCCA TGGCTTGGAG
CCCGAGGCTG GGGGCACCTT GCCCTCTCGC CTGCAGCCCA TTCTCCTCCT GGACCCCTCA
GGCTCTCATG CCCCGCTGCT GACTGTGCCC GGGCTTGGGC CCTTGCCCTT CCACTTTGCC
CAGTCCTTAA TGACCACCGA GCGGCTCTCT GGGTCAGGCC TCCACTGGCC ACTGAGCCGG
ACTCGCTCAG AGCCCCTGCC CCCCAGTGCC ACCGCTCCCC CACCGCCGGG CCCCATGCAG
CCCCGCCTGG AGCAGCTCAA AACTCACGTC CAGGTGATCA AGAGGTCAGC CAAGCCGAGT
GAGAAGCCCC GGCTGCGGCA GATACCCTCG GCTGAAGACC TGGAGACAGA TGGCGGGGGA
CCGGGCCAGG TGGTGGACGA TGGCCTGGAG CACAGGGAGC TGGGCCATGG GCAGCCTGAG
GCCAGAGGCC CCGCTCCTCT CCAGCAGCAC CCTCAGGTGT TGCTCTGGGA ACAGCAGCGA
CTGGCTGGGC GGCTCCCCCG GGGCAGCACC GGGGACACTG TGCTGCTTCC TCTGGCCCAG
```

FIG. 1ii

```
GGTGGGCACC GGCCTCTGTC CCGGGCTCAG TCTTCCCCAG CCGCACCTGC CTCACTGTCA
GCCCCAGAGC CTGCCAGCCA GGCCCGAGTC CTCTCCAGCT CAGAGACCCC TGCCAGGACC
CTGCCCTTCA CCACAGGGCT GATCTATGAC TCGGTCATGC TGAAGCACCA GTGCTCCTGC
GGTGACAACA GCAGGCACCC GGAGCACGCC GGCCGCATCC AGAGCATCTG GTCCCGGCTG
CAGGAGCGGG GGCTCCGGAG CCAGTGTGAG TGTCTCCGAG GCCGGAAGGC CTCCCTGGAA
GAGCTGCAGT CGGTCCACTC TGAGCGGCAC GTGCTCCTCT ACGGCACCAA CCCGCTCAGC
CGCCTCAAAC TGGACAACGG GAAGCTGGCA GGGCTCCTGG CACAGCGGAT GTTTGTGATG
CTGCCCTGTG GTGGGGTTGG GGTGGACACT GACACCATCT GGAATGAGCT TCATTCCTCC
AATGCAGCCC GCTGGGCCGC TGGCAGTGTC ACTGACCTCG CCTTCAAAGT GGCTTCTCGT
GAGCTAAAGA ATGGTTTCGC TGTGGTGCGG CCCCCAGGAC ACCATGCAGA TCATTCAACA
GCCATGGGCT TCTGCTTCTT CAACTCAGTG CCATCGCCT GCCGGCAGCT GCAACAGCAG
AGCAAGGCCA GCAAGATCCT CATTGTAGAC TGGGACGTGC ACCATGGCAA CGGCACCCAG
CAAACCTTCT ACCAAGACCC CAGTGTGCTC TACATCTCCC TGCATCGCCA TGACGACGGC
AACTTCTTCC CGGGGAGTGG GGCTGTGGAT GAGGTAGGGG CTGGCAGCGG TGAGGGCTTC
AATGTCAATG TGGCCTGGGC TGGAGGTCTG GACCCCCCCA TGGGGGATCC TGAGTACCTG
GCTGCTTTCA GGATAGTCGT GATGCCCATC GCCCGAGAGT TCTCTCCAGA CCTAGTCCTG
GTGTCTGCTG GATTTGATGC TGCTGAGGGT CACCCGGCCC CACTGGGTGG CTACCATGTT
TCTGCCAAAT GTTTTGGATA CATGACGCAG CAACTGATGA ACCTGGCAGG AGGCGCAGTG
GTGCTGGCCT TGGAGGGTGG CCATGACCTC ACAGCCATCT GTGACGCCTC TGAGGCCTGT
GTGGCTGCTC TTCTGGGTAA CAGGGTGGAT CCCCTTTCAG AAGAAGGCTG GAAACAGAAA
CCCAACCTCA ATGCCATCCG CTCTCTGGAG GCCGTGATCC GGGTGCACAG TAAATACTGG
GGCTGCATGC AGCGCCTGGC CTCCTGTCCA GACTCCTGGG TGCCTAGAGT GCCAGGGGCT
GACAAAGAAG AAGTGGAGGC AGTGACCGCA CTGGCGTCCC TCTCTGTGGG CATCCTGGCT
```

FIG. 1iii

```
GAAGATAGGC CCTCGGAGCA GCTGGTGGAG GAGGAAGAAC CTATGAATCT CTAAGGCTCT
GGAACCATCT GCCCGCCCAC CATGCCCTTG GGACCTGGTT CTCTTCTAAC CCCTGGCAAT
AGCCCCCATT CCTGGGTCTT TAGAGATCCT GTGGGCAAGT AGTTGGAACC AGAGAACAGC
CTGCCTGCTT TGACAGTTAT CCCAGGGAGC GTGAGAAAAT CCCTGGGTCT AGAATGGGAA
CTGGAGAGGA CCCTGAGAGG AGACGGGCTG GGCGGCGACC CCCACAGGGC TCTCGAGAAC
AGATTCTCCC CTCCAGTATG GGCCCTGGCT GTGGCCCCCA TTCCTCAGGA CTGCACAGAG
GAGGACTGGC TCCGGCTCCG TCGGGCTCAC CCTTAACCAC TATTCCTGGC TCTGCAAACC
CCAGACTTTG CACACAGCCT CAGGCTCCAC ACAGAAATGT GAACTTGGCC TCAGACAGGC
TGGCCCTTCC TAGGCTCTAG GGGCTAGGGG GGAGTGGGGA GCCAAGAGGT CCCATATTCC
TGAGTGCAGG GGTAGTCCCT CTCACCTGCT TCCTCAGACG ACTCTGGAAG CTTCCCTCTA
CCACTGGGCA CTGAGACGAA GCTCCCTGAC AGCCGAGACT GGCAGCCCTC CATCTGGTCC
GTACCCTCGC CAGAGGCCCC CCTACATCAA CCTCCTGGCG ATGCCCTGGT GGAGCAGATG
GGTGCTCTGG GAGTCCTGTG CTTCCTGATC CAATGGTGCC AAACCCTTCA TCTCCCCAAG
AAGCGCAGCA TACCCCTGGG ACCCCTCGGC CACTGCCCAC TCGGGGAGCC TTCTCTGTTT
CTGGGGCCTC CCCCACCATA GCTCTGATTC CCACCCCACA TAGGAGTAGC CTGACTGAGG
GGGAAGGGGT GGGAGAGAAG ATACAGACAT GGAGGAGGGG AGGCTGCTCT GGCAAAGTCT
TCAAGGCTTT TGGGGGTCCA GGCCTGGGGT CAAGAAGGAA AATGTGTGTG AGCATGTGTG
TGAGTGAGGC GTGTGTGTGA GCGTGTGTGT GAGTGAGGCG TGTGTGTGTG TCTTTCCTAG
GACCCACCAT ACCCTGTGTA TGTATGCATG TTTTTGTAAA AAGGAAGAAA ATGGAAAAAT
CTGAACAATA AATGTTTTAT TTGCTTTAAA AGCGAAAAAA AAAAAAAA
```

FIG. 2

```
MDLRVGQRPP VEPPPEPTLL ALQRPQRLHH HLFLAGLQQQ RSVEPMRLSM DTPMPELQVG
PQEQELRQLL HKDKSKRSAV ASSVVKQKLA EVILKKQQAA LERTVHPNSP GIPYRTLEPL
ETEGATRSML SSFLPPVPSL PSDPPEHFPL RKTVSEPNLK LRYKPKKSLE RRKNPLLRKE
SAPPSLRRRP AETLGDSSPS SSSTPASGCS SPNDSEHGPN PILGSEADSD RRTHPTLGPR
GPILGSPHTP LFLPHGLEPE AGGTLPSRLQ PILLLDPSGS HAPLLTVPGL GPLPFHFAQS
LMTTERLSGS GLHWPLSRTR SEPLPPSATA PPPPGPMQPR LEQLKTHVQV IKRSAKPSEK
PRLRQIPSAE DLETDGGGPG QVVDDGLEHR ELGHGQPEAR GPAPLQQHPQ VLLWEQQRLA
GRLPRGSTGD TVLLPLAQGG HRPLSRAQSS PAAPASLSAP EPASQARVLS SSETPARTLP
FTTGLIYDSV MLKHQCSCGD NSRHPEHAGR IQSIWSRLQE RGLRSQCECL RGRKASLEEL
QSVHSERHVL LYGTNPLSRL KLDNGKLAGL LAQRMFVMLP CGGVGVDTDT IWNELHSSNA
ARWAAGSVTD LAFKVASREL KNGFAVVRPP GHHADHSTAM GFCFFNSVAI ACRQLQQQSK
ASKILIVDWD VHHGNGTQQT FYQDPSVLYI SLHRHDDGNF FPGSGAVDEV GAGSGEGFNV
NVAWAGGLDP PMGDPEYLAA FRIVVMPIAR EFSPDLVLVS AGFDAAEGHP APLGGYHVSA
KCFGYMTQQL MNLAGGAVVL ALEGGHDLTA ICDASEACVA ALLGNRVDPL SEEGWKQKPN
LNAIRSLEAV IRVHSKYWGC MQRLASCPDS WVPRVPGADK EEVEAVTALA SLSVGILAED
RPSEQLVEEE EPMNL*
```

HISTONE DEACETYLASE AND METHODS OF USE THEREOF

CROSS-REFERENCE

This application claims the benefit of U.S. Provisional Patent Application No. 60/299,228, filed Jun. 19, 2001, which application is incorporated herein by reference in its entirety.

STATEMENT REGARDING FEDERALLY SPONSORED RESEARCH

This invention was made with U.S. government support under grant no. GM51671 awarded by the National Institutes of Health. The United States government may have certain rights in this invention.

FIELD OF THE INVENTION

This invention is in the field of gene regulation.

BACKGROUND OF THE INVENTION

The packaging of DNA into chromatin restricts the accessibility of DNA to factors involved in fundamental cellular processes such as DNA replication and transcription. The repeating organizing unit of chromatin is the nucleosome. Each nucleosome consists of a core built of two copies of histones H2A, H2B, H3, and H4, around which the DNA is tightly wrapped and bound by electrostatic interactions. Consistent with the repressive effects of chromatin on gene expression, gene activation is often accompanied by nucleosomal rearrangements. Such local or extended structural changes in chromatin are achieved by ATP-driven chromatin remodeling complexes and by posttranslational acetylation, methylation or phosphorylation of histones.

The most abundant and best-studied posttranslational modification of chromatin is the reversible acetylation of lysines in the amino-terminal tails of the four core histones. Transcriptionally silenced regions, such as heterochromatin and the inactivated mammalian X chromosome, are associated with hypoacetylated histones. In contrast, transcriptionally active domains in euchromatin are often associated with histone hyperacetylation. Localized changes in histone acetylation levels near the transcriptional start site of certain genes are linked to gene activation or repression.

The causal link between histone acetylation and transcriptional regulation is dramatically illustrated by the identification and characterization of transcriptional regulators containing histone acetyltransferase (HAT) or deacetylase (HDAC) activities. HDAC proteins are classified in three distinct families. Class I HDACs (HDAC1, 2, 3, and 8) are derived from the yeast transcriptional regulator RPD3. Class II HDACs (HDAC4, 5, 6, and 7) are similar to HDA1, another deacetylase in yeast. Class III HDACs are related to the yeast silencing protein SIR2 and are dependent on NAD for enzymatic activity. In contrast to the relative compact proteins of class I, class II HDACs (HDAC4, 5, and 7) possess two distinct domains. The carboxyl-terminal domain of HDAC4 has catalytic activity in vivo whereas the amino-terminal domain exerts autonomous repressor activity by an unknown mechanism.

Class I HDACs are expressed in most cell types; class II HDACs are expressed in a tisssue-specific manner and have been implicated in the regulation of muscle differentiation. HDACs 4 and 5 bind to transcription factors of the MEF2 family via their amino-terminal domain. This binding is regulated by calcium through calmodulin and calmodulin-dependent kinases. Both HDAC4 and HDAC5 shuttle in and out of the cell nucleus in a regulated manner controlled by phosphorylation and interaction with 14-3-3 proteins. Class II HDACs 4, 5 and 7 interact with SMRT, N-CoR, and BCoR, an additional corepressor that mediates repression by BCL-6.

HDACs are part of high-molecular-mass corepressor complexes. These complexes are recruited to specific promoters via their interactions with sequence-specific DNA binding proteins, including the nuclear hormone receptors, the E-box binding factors, and the methylcytosine-binding protein MeCP2. Class I HDAC1 and HDAC2 are found in SIN3 and NURD/Mi2 complexes. In contrast, HDAC3 is associated with the corepressors SMRT and N-CoR in a complex that mediates transcriptional repression by the thyroid hormone receptor and the oncoprotein v-ErbA.

Mutational analysis of RPD3 and HDAC1 indicates that enzymatic activity is essential for the transcriptional regulatory functions of these proteins in vivo. However, with few exceptions, it has been remarkably difficult to obtain recombinant HDAC proteins demonstrating enzymatic activity in vitro. Immunoprecipitation experiments have been required to study and characterize the enzymatic activity of most HDACs. In addition, biochemical fractionation of mammalian cell extracts has indicated that several additional proteins beside HDAC1 and HDAC2 might be necessary to build an enzymatically active HDAC1/HDAC2 core complex. The limitations observed in the expression of recombinant HDAC activity could therefore be the consequence of missing essential cofactors.

Literature

Miska et al. (1999) *EMBO J.* 18:5099-5107; Lemercier et al. (2000) *J. Biol. Chem.* 275:15594-15599; Grozinger et al. (2000) *Proc. Natl. Acad. Sci. USA* 97:7835-7840; Huynh et al. (2000) *Genes and Development* 14:1810-1823; Huang et al. (2000) *Genes Dev.* 14:45-54; Kao et al. (2000) *Genes Dev.* 14:55-66;

SUMMARY OF THE INVENTION

The present invention provides nucleic acid molecules that encode histone deacetylase, as well as recombinant vectors and host cells that include the subject nucleic acid molecules. Also provided are histone deacetylase polypeptide compositions. The histone deacteylase nucleic acid molecules are useful in a variety of diagnostic and therapeutic applications, which are also provided.

BRIEF DESCRIPTION OF THE DRAWINGS

FIG. 1 (FIG. 1*i*-1*iii*) depicts the nucleotide sequence of human HDAC7 cDNA (SEQ ID NO:01).

FIG. 2 provides the predicted amino acid sequence (SEQ ID NO:02) of the HDAC7 polypeptide encoded by the sequence provided in FIG. 1.

DEFINITIONS

Figure 3A:
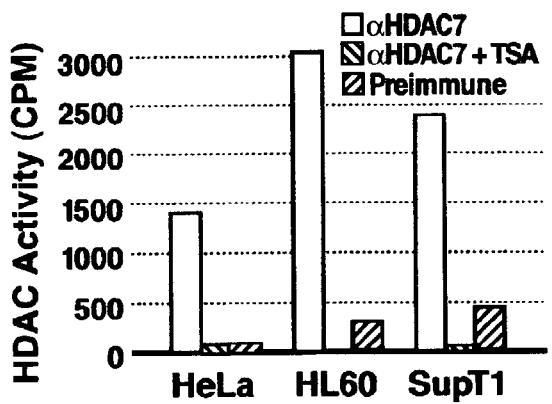
FIGS. 3A and 3B depict enzymatic activity of endogenous HDAC7.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "substantially isolated" or "isolated" polynucleotide is one that is substantially free of the sequences with which it is associated in nature. By substantially free is meant at least 50%, at least 70%, at least 80%, or at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature. In many embodiments, an isolated polynucleotide is at least about 70%, at least about 80%, at least about 90%, at least about 95%, or at least about 99%, or more, pure.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. For example, high stringency conditions include aqueous hybridization (e.g., free of formamide) in 6×SSC (where 20×SSC contains 3.0 M NaCl and 0.3 M sodium citrate), 1% sodium dodecyl sulfate (SDS) at 65° C. for about 8 hours (or more), followed by one or more washes in 0.2×SSC, 0.1% SDS at 65° C. For example, moderate stringency conditions include aqueous hybridization (e.g., free of formamide) in 6×SSC, 1% SDS at 65° C. for about 8 hours (or more), followed by one or more washes in 2×SSC, 0.1% SDS at room temperature.

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log[X^+] + 0.41(\% \, G/C) - 0.61(\% \, F) - 600/L$$

where [$X^+$] is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

| | |
|---|---|
| Mismatch Penalty: | 1.00; |
| Gap Penalty: | 1.00; |
| Gap Size Penalty: | 0.33; and |
| Joining Penalty: | 30.0. |

One parameter for determining percent sequence identity is the "percentage of the alignment region length" where the strongest alignment is found.

The percentage of the alignment region length is calculated by counting the number of residues of the individual sequence found in the region of strongest alignment. This number is divided by the total residue length of the target or query polynucleotide sequence to find a percentage. An example is shown below:

```
                                        SEQ ID NO:12
Target sequence:   GCGCGAAATACTCACTCGAGG
                        |   ||| |||| |||
Query sequence:    TATAGCCCTAC.CACTAGAGTCC
                   1    5    10   15
                                        SEQ ID NO:13
```

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vivo or in vitro with a recombinant vector or a polynucleotide of the invention. A host cell which comprises a recombinant vector of the invention is a "recombinant host cell."

The term "binds specifically," in the context of antibody binding, refers to high avidity and/or high affinity binding of an antibody to a specific polypeptide i.e., epitope of an HDAC7 polypeptide. Antibody binding to an epitope on a specific HDAC7 polypeptide (also referred to herein as "an HDAC7 epitope") is preferably stronger than binding of the same antibody to any other epitope, particularly those which may be present in molecules in association with, or in the same sample, as the specific polypeptide of interest, e.g., binds more strongly to a specific HDAC7 epitope than to a different HDAC7 epitope so that by adjusting binding conditions the antibody binds almost exclusively to the specific HDAC7 epitope and not to any other HDAC7 epitope, and not to any other HDAC7 polypeptide which does not comprise the epitope.

Antibodies which bind specifically to a subject polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, antibodies of the invention which bind to a specific HDAC7 polypeptide with a binding affinity of $10^7$ mole/l or more, e.g., $10^8$ mole/liters or more are said to bind specifically to the specific HDAC7 polypeptide. In general, an antibody with a binding affinity of $10^6$ mole/liters or less is not useful in that it will not bind an antigen at a detectable level using conventional methodology currently used.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient," used interchangeably herein, refer to a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an HDAC7 nucleic acid molecule" includes a plurality of such nucleic acid molecules and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Polypeptide Compositions

Novel histone deacetylases, as well as polypeptide compositions related thereto, are provided. The invention provides a histone deacetylase present in other than its natural environment. Novel histone deacetylases (HDAC) of the invention encompass HDAC7, and variants thereof. In some embodiments, a subject HDAC is a human HDAC, and in particular a human HDAC7 cDNA. In particular embodiments, a subject HDAC has an amino acid sequence substantially identical to the sequence of SEQ ID NO:02.

In many embodiments, a novel HDAC of the invention exhibits one or more of the following properties: (1) mRNA encoding HDAC is preferentially expressed in thymocytes; (2) enzymatic activity of the subject HDAC is dependent on interaction with HDAC3; (3) the subject HDAC forms a complex with transcriptional co-repressors SMRT and N-CoR; and (4) inhibition of HDAC levels and/or enzymatic activity induces apoptosis in cells.

The invention also provides fragments of the subject HDAC. In some embodiments, fragments exhibit histone deacetylase activity. Fragments find utility in generating antibodies to the fill-length HDAC; and in methods of screening for candidate agents that bind to and/or modulate HDAC enzymatic activity. The term "HDAC polypeptide composition" as used herein refers to both the full-length human protein as well as portions or fragments thereof. Also included in this term are variations of the naturally occurring human protein, where such variations are homologous or substantially similar to the naturally occurring protein, as described in greater detail below, as well as corresponding homologs from non-human species, such as other mammalian species. In the following description of the subject invention, the term HDAC7 is used to refer not only to the human form of this novel HDAC, but also to homologs thereof expressed in non-human species.

Human HDAC7 is a 915 amino acid protein having an amino acid sequence as shown in FIG. 2 and identified as SEQ ID NO:02. Human HDAC7 has a molecular weight based on its amino acid of about 90 to about 120 kDa.

Of particular interest in many embodiments are HDAC polypeptides, including variants of the sequence set forth in SEQ ID NO:02, fragments, and fusion proteins, that retain histone deacetylase enzymatic activity. Whether a given variant, fragment, or fusion protein exhibits histone deacetylase activity can be determined using any known assay. See, e.g., Emiliani et al. (1998) *Proc. Natl. Acad. Sci. USA* 95:2795-2800. For example, HDAC activity is measured as described in Example 1, using as substrate a chemically [$^3$H]-acetylated peptide corresponding to the amino-terminal tail of histone H4. Immobilized HDAC is suspended in 30 µl of HD buffer (10 mM Tris-HCl, pH 8.0; 10 mM Nacl; 10% glycerol) containing approximately 50,000 counts/min of the substrate. After a two-hour incubation at 37° C., the free acetate is extracted from the mixture by mixing with ethylacetylate followed by centrifugation. The amount of release acetate is measured by determining the amount of radioactivity in the supernatant using scintillation counting.

Also of interest in particular embodiments are dominant negative mutants of HDAC. Dominant negative mutants include those that inhibit the enzymatic activity of HDAC. Non-limiting examples of dominant negative mutants are: (1) amino acids 1-437 (the amino terminal domain); (2) amino acids 438-915 (the carboxyl terminal domain); and (3) amino acids 438-912.

In some embodiments, an HDAC7 polypeptide comprises the carboxyl-terminal domain exhibiting HDAC activity. Such polypeptides comprise, e.g., amino acids 438-915, or 487-912 of the sequence set forth in SEQ ID NO:02, and variants thereof. In some of these embodiments, an HDAC7 polypeptide comprising an enzymatically active carboxyl-terminal domain fused in-frame at its C-terminal or N-terminal to a heterologous (non-HDAC7) protein. Exemplary heterologous fusion partners include a a chromoprotein; a fluorescent protein; an epitope tag; an enzyme that provides for a detectable signal; a polypeptide that provides a signal for secretion of the fusion protein from a eukaryotic cell; a polypeptide that provides a signal for subcellular localization (e.g., a nuclear localization signal); a polypeptide that provides for stability of the fusion protein; and the like.

Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria Victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

In addition to the above specifically listed protein, HDAC from other species are also provided, including mammals, such as: rodents, e.g. mice, rats; domestic animals, e.g. horse, cow, dog, cat; and humans, as well as non-mammalian species, e.g. avian, and the like. By homolog is meant a protein having at least about 35%, at least about 40%, at least about 60%, at least about 70%, at least about 75%, at least about 80%, at least about 90%, at least about 95%, or at least about 98%, or higher, amino acid sequence identity to the sequence set forth in SEQ ID NO:02, as measured by using the "GAP" program (part of the Wisconsin Sequence Analysis Package available through the Genetics Computer Group, Inc. (Madison Wis.)), where the parameters are: Gap weight: 12; length weight:4. In many embodiments of interest, homology will be at least 75, usually at least 80 and more usually at least 85%, where in certain embodiments of interest homology will be as high as 90%, 95%, 98%, or higher.

Also provided are HDAC proteins that are substantially identical to the above listed proteins, where by substantially identical is meant that the protein has an amino acid sequence identity to the sequence set forth in SEQ ID NO:02 of at least about 75%, at least about 80% at least about 85%, at least about 90%, at least about 95%, or at least about 98%.

The proteins of the subject invention (e.g. HDAC7) are present in a non-naturally occurring environment, e.g. are separated from their naturally occurring environment. In certain embodiments, the subject proteins are present in a composition that is enriched for subject protein as compared to its naturally occurring environment. For example, purified HDAC are provided, where by purified is meant that the HDAC is present in a composition that is substantially free of non-HDAC proteins, where by substantially free is meant that less than 90%, usually less than 60% and more usually less than 50% of the composition is made up of non-HDAC proteins or other macromolecules. The proteins of the subject invention may also be present as an isolate, by which is meant that the protein is substantially free of other proteins and other naturally occurring biologic molecules, such as oligosaccharides, polynucleotides and fragments thereof, and the like, where substantially free in this instance means that less than 70%, usually less than 60% and more usually less than 50% of the composition containing the isolated protein is some other naturally occurring biological molecule. In certain embodiments, the proteins are present in substantially pure form, where by substantially pure form is meant at least 95%, usually at least 97% and more usually at least 99% pure.

In addition to the naturally occurring proteins, polypeptides which vary from the naturally occurring protein (e.g., HDAC7) are also provided. By HDAC7 polypeptide is meant an amino acid sequence encoded by an open reading frame (ORF) of the HDAC7 gene, described in greater detail below, including the full length HDAC7 protein and fragments thereof, particularly biologically active fragments and/or fragments corresponding to functional domains, and including fusions of the subject polypeptides to other proteins or parts thereof.

Functional domains include the carboxyl terminal domain, which exhibits histone deacetylase enzymatic activity; and the amino terminal domain, which exhibits repressor activity.

Fusion proteins may comprise a subject polypeptide, or fragment thereof, and a non-HDAC polypeptide ("the fusion partner") fused in-frame at the N-terminus and/or C-terminus of the subject HDAC polypeptide. Fusion partners include, but are not limited to, polypeptides that can bind antibody specific to the fusion partner (e.g., epitope tags); polypeptides that provide a detectable signal (e.g., a fluorescent protein, a bioluminescent protein, an enzyme that yields a detectable product, and the like); polypeptides that provide a catalytic function or induce a cellular response; polypeptides that provide for secretion of the fusion protein from a eukaryotic cell; polypeptides that provide for secretion of the fusion protein from a prokaryotic cell; and the like.

In some embodiments, an HDAC polypeptide of the invention comprises at least about 10, at least about 20, at least about 25, at least about 50, at least about 75, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, or at least about 900 contiguous amino acids (aa) of the sequence set forth in SEQ ID NO:02 and shown in FIG. 2, up to the entire amino acid sequence as set forth in SEQ ID NO:02 and shown in FIG. 2.

Fragments of the subject polypeptides, as well as polypeptides comprising such fragments, are also provided. Fragments of HDAC of interest will typically be at least about 10 aa in length, usually at least about 50 aa in length, and may be as long as 300 aa in length or longer, as described in the preceding paragraph, where the fragment will have a stretch of amino acids that is identical to the subject protein of at least about 10 aa, and usually at least about 15 aa, and in many embodiments at least about 50 aa in length.

The subject proteins and polypeptides may be obtained from naturally occurring sources or synthetically produced. Where obtained from naturally occurring sources, the source chosen will generally depend on the species from which the protein is to be derived. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may be prepared from the original source and purified using HPLC, exclusion chromatography, gel electrophoresis, immunoprecipitation of epitope-tagged HDAC, affinity chromatography, and the like.

Nucleic Acid Compositions

Also provided are nucleic acid compositions, generally isolated nucleic acids, encoding the subject novel HDAC or fragments thereof. By nucleic acid composition is meant a composition comprising a sequence of DNA having an open reading frame that encodes one the subject HDAC and is capable, under appropriate conditions, of being expressed as one of the subject HDAC described above. Thus, the term encompasses genomic DNA, cDNA, mRNA, and vectors comprising the subject nucleic acid sequences. Also encompassed in this term are nucleic acids that are homologous or substantially similar or identical to the nucleic acids encoding the subject HDAC proteins. Thus, the subject invention provides nucleic acid molecules encoding human HDAC7, and homologs thereof.

The human HDAC7 cDNA has the nucleic acid sequence shown in FIG. 1 (FIG. 1*i*-1*iii*), and identified as SEQ ID NO:01. The coding region (open reading frame) of the HDAC7 cDNA is from nucleotide 7-2751 of SEQ ID NO:01.

In some embodiments, an HDAC polynucleotide of the invention hybridizes under stringent hybridization conditions to a nucleic acid having the sequence of SEQ ID NO:01, nucleotides 7-2751 of SEQ ID NO:01, or the complement of nucleotides 7-2751 of SEQ ID NO:01.

In some embodiments, an HDAC polynucleotide of the invention has at least about 70%, at least about 75%, at least about 80%, at least about 85%, at least about 90%, at least about 95%, at least about 98%, or at least about 99% nucleotide sequence identity with the sequence set forth in SEQ ID NO:01, nucleotides 7-2751 of SEQ ID NO:01, or the complement of nucleotides 7-2751 of SEQ ID NO:01.

In some embodiments, an HDAC polynucleotide of the invention comprises a nucleotide sequence of at least about 30, at least about 50, at least about 75, at least about 100, at least about 150, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, or at least about 2700 contiguous nucleotides of the sequence set forth in SEQ ID NO:01, up to the entire coding region (open reading frame) of SEQ ID NO:01.

In other embodiments, an HDAC polynucleotide of the invention comprises a nucleotide sequence that encodes a polypeptide comprising an amino acid sequence of at least about 10, at least about 20, at least about 25, at least about 50, at least about 75, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, or at least about 900 contiguous amino acids of the amino acid sequence set forth in SEQ ID NO:2, up to the entire amino acid sequence as set forth in SEQ ID NO:2.

In other embodiments, an HDAC polynucleotide of the invention encodes a polypeptide having at least about 70%, at least about 75%, at least about 80%, at least about 85%, at least about 90%, at least about 95%, at least about 98%, or higher, amino acid sequence identity with the sequence set forth in SEQ ID NO:02.

The source of homologous genes may be any species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 60% sequence identity, usually at least 75%, more usually at least 80% between nucleotide sequences. In many embodiments of interest, homology will be at least 75, usually at least 80 and more usually at least 85%, where in certain embodiments of interest homology will be as high as 90%. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings). The sequences provided herein are essential for recognizing related and homologous proteins in database searches.

Nucleic acids encoding the proteins and polypeptides of the subject invention may be cDNA or genomic DNA or a fragment thereof. The term "HDAC nucleic acid molecule" encompasses the open reading frame encoding specific proteins and polypeptides of the subject invention, and introns, as well as adjacent 5' and 3' non-coding nucleotide sequences involved in the regulation of expression, up to about 20 kb beyond the coding region, but possibly further in either direction. The HDAC nucleic acid molecule may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a protein according to the subject invention.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

HDAC nucleic acid molecules of the invention may comprise other, non-HDAC nucleic acid molecules ("heterologous nucleic acid molecules") of any length. For example, the subject nucleic acid molecules may be flanked on the 5' and/or 3' ends by heterologous nucleic acid molecules of from about 1 nt to about 10 nt, from about 10 nt to about 20 nt, from about 20 nt to about 50 nt, from about 50 nt to about 100 nt, from about 100 nt to about 250 nt, from about 250 nt to about 500 nt, or from about 500 nt to about 1000 nt, or more in length. For example, when used as a probe to detect nucleic acid molecules capable of hybridizing with the subject nucleic acids, the subject nucleic acid molecules may be flanked by heterologous sequences of any length. Heterologous nucleic acid molecules can encode proteins or peptides such as epitope tags, signals for subcellular localization, detectable proteins (e.g., fluorescent proteins, enzymes, etc.) and the like.

The subject nucleic acid molecules may also be provided as part of a vector (e.g., an HDAC construct), a wide variety of which are known in the art and need not be elaborated upon herein. Vectors include, but are not limited to, plasmids; cosmids; viral vectors; artificial chromosomes (HACs, YACs, BACs, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject HDAC nucleic acid molecules are isolated and obtained in substantial purity, generally as other than an intact chromosome. Usually, the nucleic acid molecules will be obtained substantially free of other nucleic acid sequences that do not include a sequence or fragment thereof of the subject genes, generally being at least about 50%, at least about 80% pure, usually at least about 90% pure, at least about 95% pure, or at least about 99% pure, and are typically "recombinant", i.e. flanked by one or more nucleotides with which it is not normally associated on a naturally occurring chromosome.

Preparation of the Subject Polypeptides

In addition to the plurality of uses described in greater detail in following sections, the subject nucleic acid compositions find use in the preparation of all or a portion of the HDAC polypeptides of the subject invention, as described above. The present invention thus provides vectors ("constructs") comprising an HDAC polynucleotide of the invention, which vectors include cloning vectors and expression vectors. The present invention further provides host cells (including isolated host cells, e.g., in vitro host cells, and host cells that are part of a multicellular organism, e.g., a non-human animal) that comprise a vector of the invention.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, or any of the above-described fragment, and up to the complete open reading frame of the gene. After introduction of the construct, the cells containing the construct may be selected by means of a selectable marker, the cells expanded and then used for expression.

Proteins and polypeptides may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. Representative systems from each of these categories are provided below:

Bacteria. Expression systems in bacteria include those described in Chang et al., Nature (1978) 275:615; Goeddel et al., Nature (1979) 281:544; Goeddel et al., Nucleic Acids Res. (1980) 8:4057; EP 0 036,776; U.S. Pat. No. 4,551,433; DeBoer et al., Proc. Natl. Acad. Sci. (USA) (1983) 80:21-25; and Siebenlist et al., Cell (1980) 20:269.

Yeast. Expression systems in yeast include those described in Hinnen et al., Proc. Natl. Acad. Sci. (USA) (1978) 75:1929; Ito et al., J. Bacteriol. (1983) 153:163; Kurtz et al., Mol. Cell. Biol. (1986) 6:142; Kunze et al., J. Basic Microbiol. (1985) 25:141; Gleeson et al., J. Gen. Microbiol. (1986) 132:3459; Roggenkamp et al., Mol. Gen. Genet. (1986) 202:302; Das et al., J. Bacteriol. (1984) 158:1165; De Louvencourt et al., J. Bacteriol. (1983) 154:737; Van den Berg et al., Bio/Technology (1990) 8:135; Kunze et al., J. Basic Microbiol. (1985) 25:141; Cregg et al., Mol. Cell. Biol. (1985) 5:3376; U.S. Pat. Nos. 4,837,148 and 4,929,555; Beach and Nurse, Nature (1981) 300:706; Davidow et al., Curr. Genet. (1985) 10:380; Gaillardin et al., Curr. Genet. (1985) 10:49; Ballance et al., Biochem. Biophys. Res. Commun. (1983) 112:284-289; Tilburn et al., Gene (1983) 26:205-221; Yelton et al., Proc. Natl. Acad. Sci. (USA) (1984) 81:1470-1474; Kelly and Hynes, EMBO J. (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: The Molecular Biology Of Baculoviruses (1986) (W. Doerfler, ed.); EP 0 127,839; EP 0 155,476; and Vlak et al., J. Gen. Virol. (1988) 69:765-776; Miller et al., Ann. Rev. Microbiol. (1988) 42:177; Carbonell et al., Gene (1988) 73:409; Maeda et al., Nature (1985) 315:592-594; Lebacq-Verheyden et al., *Mol. Cell. Biol.* (1988) 8:3129; Smith et al., *Proc. Natl. Acad. Sci.* (USA) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (USA) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

The subject proteins and polypeptides may be obtained from naturally occurring sources or synthetically produced. For example, the proteins may be derived from biological sources which express the proteins. The subject proteins may also be derived from synthetic means, e.g. by expressing a recombinant gene encoding protein of interest in a suitable host, as described in greater detail infra. Any convenient protein purification procedures may be employed, where suitable protein purification methodologies are described in Guide to Protein Purification, (Deuthser ed.) (Academic Press, 1990). For example, a lysate may prepared from the original source, (e.g. a cell expressing endogenous HDAC7, or a cell comprising the expression vector expressing the subject polypeptide(s)), and purified using HPLC, exclusion chromatography, gel electrophoresis, affinity chromatography, and the like.

Compositions

The present invention further provides compositions, including pharmaceutical compositions, comprising the polypeptides, polynucleotides, antibodies, recombinant vectors, and host cells of the invention. These compositions may include a buffer, which is selected according to the desired use of the polypeptide, antibody, polynucleotide, recombinant vector, or host cell, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Antibodies Specific for an HDAC Polypeptide of the Invention

The invention provides antibodies that are specific for a subject HDAC. Suitable antibodies are obtained by immunizing a host animal with peptides comprising all or a portion of the target protein. Suitable host animals include mouse, rat sheep, goat, hamster, rabbit, etc. The origin of the protein immunogen may be mouse, human, rat, monkey etc. The host animal will generally be a different species than the immunogen, e.g. human protein used to immunize mice, etc.

The immunogen may comprise the complete protein, or fragments and derivatives thereof. Preferred immunogens comprise all or a part of one of the subject proteins, where these residues contain the post-translation modifications, such as glycosylation, found on the native target protein. Immunogens comprising the extracellular domain are produced in a variety of ways known in the art, e.g. expression of cloned genes using conventional recombinant methods, isolation from tumor cell culture supernatants, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the human protein, the animal will generally be a mouse, rat, hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, etc.

The antibody may be produced as a single chain, instead of the normal multimeric structure. Single chain antibodies are described in Jost et al. (1994) *J.B.C.* 269:26267 73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies which are identical to human antibodies may be employed. By xenogenic human antibodies is meant antibodies that are the same has human antibodies, i.e. they are fully human antibodies, with exception that they are produced using a non-human host which has been genetically engineered to express human antibodies. See e.g. WO 98/50433; WO 98,24893 and WO 99/53049, the disclosures of which are herein incorporated by reference.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Uses of the Subject Polypeptide and Nucleic Acid Compositions

The subject polypeptide and nucleic acid compositions find use in a variety of different applications, including research, diagnostic, and therapeutic agent screening/discovery/preparation applications, as well as therapeutic compositions.

General Applications

The subject nucleic acid compositions find use in a variety of different applications. Applications of interest include: the identification of homologs of the subject HDAC; as a source of novel promoter elements; the identification of expression regulatory factors; as probes and primers in hybridization applications, e.g. polymerase chain reaction (PCR); the identification of expression patterns in biological specimens; the preparation of cell or animal models for function of a subject HDAC; the preparation of in vitro models for function of the subject HDAC; etc.

Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided nucleic acid sequences, e.g. allelic variants, genetically altered versions of the gene, etc., bind to the provided nucleic acid molecules under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where the subject genes are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194-205; Mortlock et al. (1996), *Genome Res.* 6:327-33; and Joulin and Richard-Foy (1995), *Eur. J. Biochem.* 232:620-626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to a gene in order to promote expression of wild type or proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of gene expression in the sample.

The sequence of a gene according to the subject invention, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated genes may be used to study structure-function relationships of the subject proteins, or to alter properties of the protein that affect its function or regulation.

The subject nucleic acids can be used to generate transgenic, non-human animals or site-specific gene modifications in cell lines. Thus, in some embodiments, the invention provides a non-human transgenic animal comprising, as a transgene integrated into the genome of the animal, a nucleic acid molecule comprising a sequence encoding a subject HDAC in operable linkage with a promoter, such that the HDAC-encoding nucleic acid molecule is expressed in a cell of the animal. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

The modified cells or animals are useful in the study of gene function and regulation. For example, a series of small deletions and/or substitutions may be made in the host's native gene to determine the role of different exons in oncogenesis, signal transduction, etc. Of interest is the use of genes to construct transgenic animal models for cancer, where expression of the subject protein is specifically reduced or absent. Specific constructs of interest include antisense constructs, which will block expression, expression of dominant negative mutations, and over-expression of genes. Where a sequence is introduced, the introduced sequence may be either a complete or partial sequence of a gene native to the host, or may be a complete or partial sequence that is exogenous to the host animal, e.g., a human sequence of the subject invention. A detectable marker, such as lac Z may be introduced into the locus, where upregulation of expression will result in an easily detected change in phenotype.

One may also provide for expression of the HDAC cDNA, e.g. the human HDAC7 cDNA, or variants thereof in cells or tissues where it is not normally expressed, at levels not normally present in such cells or tissues, or at abnormal times of development. One may also generate host cells (including host cells in transgenic animals) that comprise a heterologous nucleic acid molecule which encodes a polypeptide which functions to modulate expression of an endogenous human HDAC7 promoter or other transcriptional regulatory region.

DNA constructs for homologous recombination will comprise at least a portion of the human gene or of a gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

The present invention provides transgenic non-human animals comprising, as a transgene, an HDAC polynucleotide of the invention. Numerous publications are available that teach how to make transgenic animals, including, e.g., *Transgenesis Techniques: Principles and Protocols* D. Murphy and D. A. Carter, ed. (June 1993) Humana Press; *Transgenic Animal Technology: A Laboratory Handbook* C. A. Pinkert, ed. (January 1994) Academic Press; *Transgenic Animals* F. Grosveld and G Kollias, eds. (July 1992) Academic Press; and *Embryonal Stem Cells: Introducing Planned Changes into the Animal Germline* M. L. Hooper (January 1993) Gordon & Breach Science Pub.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on human HDAC7 activity.

Diagnostic Applications

The present invention provides a variety of diagnostic assays. Such assays include methods to detect HDAC mRNA, protein, and enzymatic activity in a biological sample; and screening methods to identify agents that modulate a level of mRNA, protein, or enzymatic activity. Of particular interest are diagnostic applications using or detecting HDAC7 mRNA, protein, and enzymatic activity. Accordingly, in the following sections, diagnostic methods using or detecting "HDAC" mRNA, protein, and enzymatic activity apply to methods of detecting HDAC7 mRNA, protein, and enzymatic activity.

Also provided are methods of diagnosing disease states based on observed levels of the subject HDAC or the expression level of the subject nucleic acid molecules in a biological sample of interest. Samples, as used herein, include biological fluids such as blood, cerebrospinal fluid, tears, saliva, lymph, dialysis fluid, semen and the like; cells; organ or tissue culture derived fluids; tumor biopsy samples; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Detection methods of the invention may be qualitative or quantitative. Thus, as used herein, the terms "detection," "determination," and the like, refer to both qualitative and quantitative determinations, and include "measuring."

Detection methods of the present invention include methods for detecting HDAC polypeptide in a biological sample, methods for detecting HDAC mRNA in a biological sample, and methods for detecting HDAC enzymatic activity in a biological sample.

Of particular interest in some embodiments is use of detection methods to detect HDAC protein and/or mRNA and/or enzymatic activity as a marker for cancerous cells. For example, cancerous cells are expected to exhibit an elevated level of HDAC protein and/or mRNA and/or enzymatic activity. Accordingly, the invention further provides methods of identifying a cancerous cell in a population of cells (which population of cells is a mixed population comprising a cancerous cell(s) and non-cancerous cells), comprising detecting HDAC protein and/or mRNA and/or enzymatic activity in the population of cells, as described further below. Of particular interest in some embodiments is the detection of tumors of lymphoid origin including lymphomas, leukemias, thymomas and other related tumors.

In addition, because of its ability to regulate apoptosis, inappropriate expression of HDAC7 in any tumor could potentially contribute to the tumoral phenotype. Accordingly, it is conceivable that HDAC7 overexpression could be associated to any tumor. Because HDAC7 is expressed during T cell development at a time when T cells learn to distinguish self from nonself (thymic negative selection) overexpression or inappropriate expression of HDAC7 could lead to selective dysregulation of the immune system such as autoimmune diseases or immune deficiencies. In the case of autoimmune diseases, such diagnostic assay is useful for diseases such as juvenile diabetes, multiple sclerosis, systemic lupus erythematosus, rheumatoid arthritis and other related disorders.

The detection methods can be provided as part of a kit. Thus, the invention further provides kits for detecting the presence and/or a level of HDAC polypeptide or HDAC polynucleotides or HDAC enzymatic activity in a biological sample. Procedures using these kits can be performed by clinical laboratories, experimental laboratories, medical practitioners, or private individuals. The kits of the invention for detecting an HDAC polypeptide comprise a moiety that specifically binds HDAC, including, but not limited to, an HDAC-specific antibody. The kits of the invention for detecting an HDAC polynucleotide comprise a moiety that specifically hybridizes to an HDAC polynucleotide. The kit may optionally provide additional components that are useful in the procedure, including, but not limited to, buffers, developing reagents, labels, reacting surfaces, means for detections, control samples, standards, instructions, and interpretive information.

Methods of Detecting an HDAC Polypeptide in a Biological Sample

The present invention further provides methods for detecting the presence and/or measuring a level of an HDAC polypeptide in a biological sample, using an HDAC-specific antibody. The methods generally comprise:

a) contacting the sample with an antibody specific for an HDAC polypeptide; and b) detecting binding between the antibody and molecules of the sample.

Detection of specific binding of the HDAC-specific antibody, when compared to a suitable control, is an indication that HDAC polypeptides are present in the sample. Suitable controls include a sample known not to contain an HDAC polypeptide; and a sample contacted with an antibody not specific for HDAC, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the HDAC-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (a green fluorescent protein), and the like. The antibody may be attached (coupled) to an insoluble support, such as a polystyrene plate or a bead. Indirect labels include second antibodies specific for HDAC-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled HDAC7-specific antibody. Detection methods are known in the art and will be chosen as appropriate to the signal emitted by the detectable label. Detection is generally accomplished in comparison to suitable controls, and to appropriate standards.

Methods of Detecting an HDAC mRNA in a Biological Sample

The present invention further provides methods for detecting the presence of HDAC mRNA in a biological sample. The methods can be used, for example, to assess whether a test compound affects HDAC gene expression, directly or indirectly.

The methods generally comprise:

a) contacting the sample with an HDAC polynucleotide of the invention under conditions which allow hybridization; and b) detecting hybridization, if any.

Detection of hybridization, when compared to a suitable control, is an indication of the presence in the sample of an HDAC polynucleotide. Appropriate controls include, for example, a sample which is known not to contain HDAC mRNA, and use of a labeled polynucleotide of the same "sense" as an HDAC mRNA. Conditions which allow hybridization are known in the art, and have been described in more detail above. Detection can be accomplished by any known method, including, but not limited to, in situ hybridization, PCR, RT-PCR, and "Northern" or RNA blotting, or combinations of such techniques, using a suitably labeled HDAC polynucleotide. A variety of labels and labeling methods for polynucleotides are known in the art and can be used in the assay methods of the invention. Specific hybridization can be determined by comparison to appropriate controls.

Methods using PCR amplification can be performed on the DNA from a single cell, although it is convenient to use at least about $10^5$ cells. The use of the polymerase chain reaction is described in Saiki et al. (1985) *Science* 239:487, and a review of current techniques may be found in Sambrook, et al. *Molecular Cloning: A Laboratory Manual*, CSH Press 1989, pp.14.2-14.33. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g $^{32}$p, $^{35}$S, $^{3}$H, etc. The label may be a two stage system, where the amplified DNA is conjugated to biotin, haptens, etc. having a high affinity binding partner, e.g avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A number of methods are available for determining the expression level of a gene or protein in a particular sample. Diagnosis may be performed by a number of methods to determine the absence or presence or altered amounts of normal or abnormal HDAC in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of the subject HDAC nucleic acid molecules. Biochemical studies may be performed to determine whether a sequence polymorphism in a coding region or control regions is associated with disease. Disease associated polymorphisms may include deletion or truncation of the gene, mutations that alter expression level, that affect the activity of the protein, etc.

Changes in the promoter or enhancer sequence that may affect expression levels of the subject genes can be compared to expression levels of the normal allele by various methods known in the art. Methods for determining promoter or enhancer strength include quantitation of the expressed natural protein; insertion of the variant control element into a vector with a reporter gene such as P-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express the gene may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), Science 239:487, and a review of techniques may be found in Sambrook, et al. *Molecular Cloning: A Laboratory Manual*, CSH Press 1989, pp.14.2-14.33. Alternatively, various methods are known in the art that utilize oligonucleotide ligation as a means of detecting polymorphisms, for examples see Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in the gene may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity of the encoded protein may be determined by comparison with the wild-type protein.

Diagnostic methods of the subject invention in which the level of expression is of interest will typically involve comparison of the nucleic acid abundance of a sample of interest with that of a control value to determine any relative differences, where the difference may be measured qualitatively and/or quantitatively, which differences are then related to the presence or absence of an abnormal expression pattern. A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The present invention provides screening methods for identifying agents which modulate HDAC enzyme activity, methods for identifying agents which modulate a level of a subject HDAC polypeptide in a cell; and methods for identifying agents which modulate a level of a subject HDAC mRNA in a cell; and methods for identifying agents that modulate release of a subject HDAC from a eukaryotic cell. In some embodiments, the assay is a cell-free assay. In other embodiments, the assay is a cell-based assay.

As used herein, the term "modulate" encompasses "increase" and "decrease." In some embodiments, of particular interest are agents which inhibit HDAC activity, and/or which reduce a level of a subject HDAC polypeptide in a cell, and/or which reduce a level of a subject HDAC mRNA in a cell and/or which reduce release of a subject HDAC from a eukaryotic cell. Such agents are of interest as candidates for treating cancers.

The terms "candidate agent," "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Methods for Identifying Agents that Modulate HDAC Activity

The present invention provides methods of identifying agents which modulate an enzymatic activity of an HDAC polypeptide of the invention. The term "modulate" encompasses an increase or a decrease in the measured HDAC activity when compared to a suitable control.

The method generally comprises:

a) contacting a test agent with a sample containing an HDAC polypeptide; and b) assaying an HDAC activity of the HDAC polypeptide in the presence of the substance. An increase or a decrease in HDAC activity in comparison to HDAC activity in a suitable control (e.g., a sample comprising an HDAC polypeptide in the absence of the substance being tested) is an indication that the substance modulates an enzymatic activity of the HDAC.

An "agent which modulates an HDAC activity of an HDAC polypeptide", as used herein, describes any molecule, e.g. synthetic or natural organic or inorganic compound, protein or pharmaceutical, with the capability of altering an HDAC activity of an HDAC polypeptide, as described herein. Generally a plurality of assay mixtures is run in parallel with different agent concentrations to obtain a differential response to the various concentrations. Typically, one of these concentrations serves as a negative control, i.e. at zero concentration or below the level of detection.

HDAC activity can be measured using any assay known in the art. For example, HDAC activity is measured as described in Example 1, using as substrate a chemically [$^3$H]-acetylated peptide corresponding to the amino-terminal tail of histone H4. Immobilized HDAC is suspended in 30 μl of HD buffer (10 mM Tris-HCl, pH 8.0; 10 mM Nacl; 10% glycerol) containing approximately 50,000 counts/min of the substrate. After a two-hour incubation at 37° C., the immobilized HDAC is separated from the reaction mixture, e.g., by centrifugation and the amount of release acetate is measured by determining the amount of radioactivity in the supernatant.

An agent which modulates an HDAC activity of a subject polypeptide increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

Agents that increase or decrease an HDAC activity of a subject polypeptide to the desired extent may be selected for further study, and assessed for cellular availability, cytotoxicity, biocompatibility, etc.

Of particular interest are agents that decrease an HDAC activity of a subject polypeptide. Maximal inhibition of HDAC activity is not always necessary, or even desired, in every instance to achieve a therapeutic effect. Agents which decrease an HDAC activity of a subject polypeptide are useful in inducing apoptosis in cancerous cells, particular cancerous thymocytes, and thus may be useful in treating cancers. Where inappropriate expression of HDAC7 occurs, inhibition of HDAC7 leads to specific inhibition of tumor growth or selective killing of tumor cells expressing high levels of HDAC7.

Cell-Based Methods

Cell-based methods include methods of detecting an agent that modulates a level of a subject HDAC mRNA and/or subject HDAC polypeptides, and methods for detecting an agent that modulates release of a subject HDAC from a eukaryotic cell.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cell cultures or may be immortalized cell lines.

Methods of Detecting Agents that Modulate a Level of HDAC mRNA and/or HDAC Polypeptide A wide variety of cell-based assays may be used for identifying agents which modulate levels of HDAC mRNA and for identifying agents that modulate release of an HDAC from a eukaryotic cell, using, for example, a mammalian cell transformed with a construct comprising an HDAC-encoding cDNA such that the cDNA is overexpressed, or, alternatively, a construct comprising an HDAC promoter operably linked to a reporter gene.

Accordingly, the present invention provides a method for identifying an agent, particularly a biologically active agent, that modulates a level of HDAC expression in a cell, the method comprising: combining a candidate agent to be tested with a cell comprising a nucleic acid which encodes an HDAC polypeptide; and determining the effect of said agent on HDAC expression. "Modulation" of HDAC expression levels includes increasing the level and decreasing the level of HDAC mRNA and/or HDAC polypeptide encoded by the HDAC polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of HDAC mRNA and/or polypeptide following contacting the cell with a candidate agent being tested, compared to a control to which no agent is added, is an indication that the agent modulates HDAC expression.

HDAC mRNA and/or polypeptide whose levels are being measured can be encoded by an endogenous HDAC polynucleotide, or the HDAC polynucleotide can be one that is comprised within a recombinant vector and introduced into the cell, i.e., the HDAC mRNA and/or polypeptide can be encoded by an exogenous HDAC polynucleotide. For example, a recombinant vector may comprise an isolated HDAC transcriptional regulatory sequence, such as a promoter sequence, operably linked to a reporter gene (e.g,. β-galactosidase, CAT, luciferase, or other gene that can be easily assayed for expression). In these embodiments, the method for identifying an agent that modulates a level of HDAC expression in a cell, comprises: combining a candidate agent to be tested with a cell comprising a nucleic acid which comprises an HDAC gene transcriptional regulatory element operably linked to a reporter gene; and determining the effect of said agent on reporter gene expression.

A recombinant vector may comprise an isolated HDAC transcriptional regulatory sequence, such as a promoter sequence, operably linked to sequences coding for an HDAC polypeptide; or the transcriptional control sequences can be operably linked to coding sequences for an HDAC fusion protein comprising HDAC polypeptide fused to a polypeptide which facilitates detection. In these embodiments, the method comprises combining a candidate agent to be tested with a cell comprising a nucleic acid which comprises an HDAC gene transcriptional regulatory element operably linked to an HDAC polypeptide-coding sequence; and determining the effect of said agent on HDAC expression, which determination can be carried out by measuring an amount of HDAC mRNA, HDAC polypeptide, or HDAC fusion polypeptide produced by the cell.

Cell-based assays generally comprise the steps of contacting the cell with an agent to be tested, forming a test sample, and, after a suitable time, assessing the effect of the agent on HDAC expression. A control sample comprises the same cell without the candidate agent added. HDAC expression levels are measured in both the test sample and the control sample. A comparison is made between HDAC expression level in the test sample and the control sample. HDAC expression can be assessed using conventional assays. For example, when a mammalian cell line is transformed with a construct that results in expression of HDAC, HDAC mRNA levels can be detected and measured, as described above, or HDAC polypeptide levels can be detected and measured, as described above. A suitable period of time for contacting the agent with the cell can be determined empirically, and is generally a time sufficient to allow entry of the agent into the cell and to allow the agent to have a measurable effect on HDAC mRNA and/or polypeptide levels. Generally, a suitable time is between 10 minutes and 24 hours, more typically about 1-8 hours.

Methods of measuring HDAC mRNA levels are known in the art, several of which have been described above, and any of these methods can be used in the methods of the present invention to identify an agent which modulates HDAC mRNA level in a cell, including, but not limited to, a PCR, such as a PCR employing detectably labeled oligonucleotide primers, and any of a variety of hybridization assays. Similarly, HDAC polypeptide levels can be measured using any standard method, several of which have been described herein, including, but not limited to, an immunoassay such as ELISA, for example an ELISA employing a detectably labeled antibody specific for an HDAC polypeptide, e.g., for an epitope-tagged HDAC polypeptide.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4 and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Nucleic Acid and Polypeptide Therapeutic Compositions

The nucleic acid compositions of the subject invention also find use as therapeutic agents in situations where one wishes to enhance HDAC activity in a host, particularly the activity of the subject polypeptides. The subject genes, gene fragments, or the encoded proteins or protein fragments are useful in gene therapy to treat disorders associated with defects in the genes encoding the subject HDAC. Nucleic acid molecules encoding dominant negative mutants of HDAC7 are useful to reduce, inhibit, or reverse adverse effects of overexpression of HDAC7.

Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Therapeutic Methods

The instant invention provides various therapeutic methods. In some embodiments, methods of regulating, including modulating and inhibiting, enzymatic activity of the subject proteins are provided. The subject methods find use in the treatment of a variety of different disease conditions involving the subject HDAC. Such disease conditions include tumors of lymphoid origin. Thus, the subject methods are useful for treating tumors of lymphoid origin. In some of these embodiments, methods are provided for reducing tumor growth. Furthermore, where overexpression of HDAC7 leads to development of autoimmune disorders, or immune deficiencies, reduction in HDAC7 levels and/or activity is useful to treat autoimmune disorders and immune deficiencies.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

As used herein, the term "agent" refers to a substance that modulates a level of enzymatically active subject HDAC. In some embodiments, an agent is one identified by a screening assay of the invention. "Modulating a level of enzymatically active subject HDAC" includes increasing or decreasing enzymatic activity of a subject HDAC; increasing or decreasing a level of enzymatically active HDAC protein; and increasing or decreasing a level of mRNA encoding enzymatically active subject HDAC.

Methods of reducing tumor growth, and methods of reducing subject HDAC activity, generally comprise administering to an individual an agent that reduces a level of enzymatically active subject HDAC.

Tumors which may be treated using the methods of the instant invention include, but are not limited to, hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; thymomas, and any tumor in which HDAC7 overexpression contributes to the tumoral phenotype.

In addition, because of its ability to regulate apoptosis, inappropriate expression of HDAC7 in any tumor could potentially contribute to the tumoral phenotype. Accordingly, it is conceivable that HDAC7 overexpression could be associated to any tumor. Because HDAC7 is expressed during T cell development at a time when T cells learn to distinguish self from nonself (thymic negative selection) overexpression or inappropriate expression of HDAC7 could lead to selective dysregulation of the immune system such as autoimmune diseases or immune deficiencies. In the case of autoimmune diseases, inhibition of HDAC7 activity or expression might be useful for diseases such as juvenile diabetes, multiple sclerosis, systemic lupus erythematosus, rheumatoid arthritis and other related disorders.

Whether tumor cell growth is inhibited or reduced can be assessed by any means known in the art, including, but not limited to, measuring tumor size; determining whether tumor cells are proliferating, e.g., by using a $^3$H-incorporation assay; and/or counting tumor cells.

In some embodiments, an agent is administered to the individual that stimulates or promotes apoptosis in a tumor cell. Agents include, but are not limited to, a dominant negative mutant of HDAC, an agent identified using a screening method of the invention, etc. A construct that includes a dominant negative mutant is generated such that the mutant-encoding sequences are under transcriptional control of a thymocyte-specific promoter and optionally other regulatory elements. Such a construct is expected to induce apoptosis in thymocytes.

Apoptosis can be assayed using any known method. Assays can be conducted on cell populations or an individual cell, and include morphological assays and biochemical assays. A non-limiting example of a method of determining the level of apoptosis in a cell population is TUNEL (TdT-mediated dUTP nick-end labeling) labeling of the 3'-OH free end of DNA fragments produced during apoptosis (Gavrieli et al. (1992) *J. Cell Biol.* 119:493). The TUNEL method consists of catalytically adding a nucleotide, which has been conjugated to a chromogen system or a to a fluorescent tag, to the 3'-OH end of the 180-bp (base pair) oligomer DNA fragments in order to detect the fragments. The presence of a DNA ladder of 180-bp oligomers is indicative of apoptosis. Procedures to detect cell death based on the TUNEL method are available commercially, e.g., from Boehringer Mannheim (Cell Death Kit) and Oncor (Apoptag Plus). Another marker that is currently available is annexin, sold under the trademark APOPTESTJ. This marker is used in the "Apoptosis Detection Kit," which is also commercially available, e.g., from R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PI, necrotic cells stain positive for both, live cells stain negative for both. Other methods of testing for apoptosis are known in the art and can be used, including, e.g., the method disclosed in U.S. Pat. No. 6,048,703.

Dosages, Routes of Administration, and Formulations

As mentioned above, an effective amount of the active agent is administered to the host, where "effective amount" means a dosage sufficient to produce a desired result. generally, the desired result is at least a reduction in enzymatic activity of a subject HDAC as compared to a control.

In the subject methods, the active agent(s) may be administered to the host using any convenient means capable of resulting in the desired inhibition of HDAC activity. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal,etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the therapeutic DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations are used, e.g., s, seconds; min, minutes; h, hours; aa, amino acids; bp, base pairs, etc.

Example 1

Cloning and Characterization of Histone Deacetylase-7

Materials and Methods

Plasmids and Recombinant DNA—Computer algorithms for predicting exon-intron boundaries (Genscan (Burge et al. (1997) *J. Mol. Biol.* 268:78-94); GenFinder (Solovyev et al. (1997) *Ismb* 5:294-302)) and sequence similarity of HDAC7 to HDAC4 and HDAC5 were used to deduce a putative ORF derived from a genomic sequence located at chromosome 12q31 (GenBank AC0004466). Overlapping human cDNA fragments were amplified from a HeLa cell cDNA library (Clontech) using the following primer pairs:

```
                                         (SEQ ID NO:03)
5'-CGGAATTCCAGCCCATGGACCTGCGGGTG-3'  and (SEQ ID NO:04)
5'-CGGAATTCGACCGAGTCATAGATCAGCC-3';

(SEQ ID NO:05)
5'-CGGAATTCACCATGGCCCCGCTGCTGACTGTGCC-3'  and (SEQ ID NO:06)
5'-CGGAATTCGAGATTCATAGGTTCTTCCTC.
```

The full length HDAC7 ORF was generated using a unique Bcl I site in these fragments and the resulting cDNA was extended in 5' and 3' directions by anchored PCR strategies (rapid amplification of cDNA ends, RACE). Nucleotide sequencing on both strands was performed using the dideoxy sequencing method (ABI bioprism). FLAG-tagged expression vectors for different HDACs were generated as previously described. Fischle et al. (1999) *J. Biol. Chem.* 274: 11713-11720. HDAC5 cDNA was obtained as an expressed sequence tag (EST) clone (Id 1142916) from the I.M.A.G.E. Consortium, and the sequence corresponding to nucleotides 394-3369 of the HDAC5 ORF was used to construct the fusion protein. Grozinger et al. (1999) *Proc. Natl. Acad. Sci. USA* 96:4868-4873. HDAC6 was cloned from a human cDNA library (Clontech) with primers corresponding to the sequence from GenBank entry AJ011972 (defined as a transcription map in Xp11). The sequence of this ORF is identical to that of HDAC6 (Grozinger et al. (1999) *Proc. Natl. Acad. Sci. USA* 96:4868-4873). Deletion constructs were generated by standard procedures (Sambrook, J., Maniatis, T., and Fritsch, E. F. (1989) *Molecular cloning: A laboratory manual,* 2nd eds, pp. 3 v., Cold Spring Harbor Laboratory, Cold Spring Harbor, N.Y.; Ausubel, F. M., Brent, R., Kingston, R. E., Moore, D. D., Seidman, J. G., Smith, J. A., and Struhl, K. (1995) *Current Protocols in Molecular Biology,* eds, 1, pp. John Wiley & Sons, Inc., New York). EcoRI fragments from the pcDNA3.1 expression constructs were subcloned into the EcoRI site of pGEX4T1 (Pharmacia), to generate amino-terminal GST fusion proteins.

Northern Blot Analysis—A multiple human tissue northern blot was obtained from CLONTECH. [$^{32}$P]-labeled probes corresponding to hHDAC7 and hGAPDH cDNAs were prepared with the Multiprime DNA labeling system (Amersham). Blots were prehybridized and hybridized with ExpressHyb hybridization solution (Clontech) and washed under high-stringency conditions. (Maniatis, T., Fritsch, E. F., and Sambrook, J. (1989) *Molecular Cloning: A Laboratory Manual,* 2nd eds, pp. Cold Spring Harbor Laboratory, Cold Spring Harbor). Autoradiographs were analyzed with a FUJIX BAS1000 phosphorimaging system (Fuji, Tokyo, Japan).

Generation of Antibodies—cDNA fragments corresponding to amino acids (aa) 118-662 of hHDAC4 and aa 1-487 of hHDAC7 were cloned into the pGEX4T1 vector (Pharmacia) to generate hybrid proteins fused to GST. Fusion proteins were expressed in BL21 RIP (Stratagene), purified according to standard procedures (Pharmacia) and separated from co-purified contaminating bacterial proteins by large-scale preparative sodium dodecyl sulfate-polyacrylamide gel electrophoresis (SDS-PAGE). Antisera against the recombinant proteins were raised in New Zealand white rabbits according to standard procedures (Harlan Bioproducts). To eliminate antibody species with affinity for GST and to reduce putative crossreactivity, antisera were depleted on GST and ortholog GST-HDAC columns (e.g., HDAC7 antiserum was depleted on GST HDAC4 columns) followed by purification of the IgG species according to standard protocols (Harlow, E., and Lane, D. (1988) *Antibodies: A Laboratory Manual*, eds, pp. Cold Spring Harbor Laboratory, Cold Spring Harbor).

Immunoprecipitation—Immunoprecipitation was performed as previously described. Fischle et al. (1999) *J. Biol. Chem.* 274:11713-11720). For FLAG-tagged proteins, M2 agarose (Sigma) was used at 15 µl/ml. For precipitation of endogenous proteins, the polyclonal anti-HDAC4 and anti-HDAC7 antisera were used at approximately 10 µg/ml in combination with 20 µl/ml of a preblocked (10 mg/ml BSA) 50% protein G-Sepharose slurry (Amersham).

SDS-PAGE and Western Blotting—SDS-PAGE and western blot analysis were performed according to standard procedures (Ausubel, supra). Western blots were developed with ECL (Amersham). Polyclonal anti-HDAC1 and anti-HDAC3 antisera have been described previously (Emiliani et al. (1998) *Proc. Natl. Acad. Sci. USA* 95:2795-2800). Polyclonal anti-IKKα, anti-SIN3, anti-HDAC2 and anti-FLAG antisera used were from Santa Cruz Biotechnology (Santa Cruz, Calif.). SMRT and N-CoR antibodies were from Upstate Biotech (Lake Placid, N.Y.) and ABR (Golden, Colo.).

Histone Deacetylase Activity Assays—HDAC activity was measured with a chemically [$^3$H]-acetylated peptide corresponding to the amino-terminal tail of histone H4 as previously described (Fischle et al. supra). Complexes immobilized on beads either from immunoprecipitations or GST pull-down assays were resuspended in 30 µl of HD buffer containing approximately 50,000 counts/min of the substrate.

Preparation of nuclear and cytoplasmic extracts—Cell nuclei were isolated and lysed according to Osborn with slight modifications (Osborn et al. (1989) *Proc. Natl. Acad. Sci. USA* 86:2336-2340).

Immunofluorescence and Confocal Microscopy—Cells were plated onto glass coverslips and transfected the following day with Lipofectamine 2000 (Life Technologies) according to the manufacturer's instructions. After incubation overnight, transfected cells were fixed with 1% paraformaldehyde, permeabilized with phosphate buffered saline (PBS), pH 7.2 and 0.5% Triton X-100 and then incubated for 60 min at room temperature with the appropriate antibodies at dilutions typically between 1:100 and 1:1000. Cells were mounted onto glass slides in PBS/90% glycerol containing 1 mM paraphenylenediamine as an antifade reagent. Confocal microscopy was performed with a Zeiss LSM510 laser scanning confocal microscope at 488 nm (Alexa 488—conjugated secondary antibodies) and 543 nm (Cy3-conjugated secondary antibodies). The pinhole aperture was set to 1.0 airy unit for each channel. Band-pass filters and sequential scanning of individual fluorescent probes were used to eliminate cross talk between channels. Images were collected as 12-bit images, and each channel was independently rescaled from 0 to 255 (8-bit) for final presentation.

GST Fusion Proteins: Expression and Pulldown Assays—Fusion proteins were expressed in DH5α (Life Technologies) or BL21 RIP (Stratagene) and purified according to standard protocols (Pharmacia). Purity, as well as protein amount, was checked on SDS-PAGE gels stained with Coomassie Blue. For pulldown reactions, extracts from 293, HeLa, A301, or SupTI cells were used (Fischle et al., supra; Dignam et al. (1983) Methods Enzymol. 101:582-598). After incubation for 3 hours at 4° C. with rocking, reactions were washed three times in IPLS, three times in the same buffer but at 1 M NaCl, and two times in HD buffer (Fischle et al., supra). Pulldown reactions were split, and either processed for histone deacetylase activity assays or for western blotting. For pulldown reactions with $^{35}$S-labeled proteins, cDNAs were transcribed and translated with the TNT reticulocyte system (Promega). The labeling reaction (5 µl) was incubated with GST fusion proteins in a total volume of 200 µl of GST buffer (20 mM Tris-HCl, pH 8.0, 150 mM KCl, 5 mM DTT, 2 mM EDTA, 10% glycerol, 0.5% non fat dry milk, 0.1% NP-40) for 1 h at 4° C. with rocking. Reactions were washed five times in the same buffer, and bound proteins were resolved on denaturing SDS-PAGE gels for analysis by autoradiography.

Results

HDAC7, a New Member of the Human Class II HDAC family—We previously identified a new human genomic sequence, located on chromosome 12q31 (GenBank AC0004466), which potentially encoded a new human class II HDAC (Fischle et al., supra). Two different computer algorithms for the prediction of exon-intron boundaries (Genscan; GenFinder) and the sequence similarity to HDAC4 and HDAC5 were used to deduce a putative cDNA encoded by this locus. Based on this information we devised a PCR strategy in combination with 5' and 3' rapid amplification of cDNA ends (RACE) reactions to clone several cDNAs sharing an open reading frame (ORF) of 2745 base pairs but different 5' extremities. The amplified cDNAs contained a single putative start codon embedded in a sequence environment favorable for the initiation of translation and in-frame with an upstream stop codon. The nucleotide sequence is provided in FIG. 1 (FIG. 1i-1iii). The corresponding ORF translated to a putative polypeptide of 915 amino acids (aa), as shown in FIG. 2.

The same polypeptide originating from the 12q31 locus was independently predicted by the Human Genome Project (GenBank XP-007047). Interestingly, the amino-terminus of human HDAC7 is 22 aa shorter than that of murine HDAC7, despite >95% conservation of the rest of the protein (Kao et al. (2000) Genes Dev. 14:55-66). A five-amino acid motif, P-X-D-L-R, (Zhang et al. (2001) J. Biol. Chem. 276:35-39) conserved in HDAC4, HDAC5, and hMITR, implicated in the interaction with the transcriptional corepressor CtBP is missing in the human HDAC7 protein. As previously reported for other class II HDACs, HDAC7 contains two distinct domains. The carboxyl-terminal domain (aa 438-915) shows high homology to known HDACs, in particular class II HDACs. The amino-terminal domain is related to similar regions in HDAC4, HDAC5 and hMITR, as shown in the data provided in Table 1.

TABLE 1

|  | HDAC1 | HDAC2 | HDAC3 | HDAC4 C-term (612-1084) | HDAC5 C-term (648-1122) |
|---|---|---|---|---|---|
| HDAC7 C-term (438-915) | 40% | 40% | 41% | 81% | 79% |

|  | HDAC4 N-term (1-611) | HDAC5 N-term (1-647) | hMITR (KIAA0744) |
|---|---|---|---|
| HDAC7 N-term (1-487) | 31% | 36% | 33% |
| HDAC7 N-term (1-611) |  | 45% | 47% |

The expression of HDAC7 in different tissues was examined by northern blot on multiple tissues. A major transcript of 4.4 kilobases (kb) was detected mainly in heart and placenta, but also in pancreas, lung and skeletal muscle. A weaker band corresponding to 6.0 kb might represent a differentially spliced isoform of the HDAC7 mRNA. The size of 4.4 kb is in good agreement with the lengths of several cDNAs cloned.

HDAC7 is a Predominantly Nuclear Protein and Localizes to Discrete Foci in the Cell Nucleus—To examine the subcellular localization of the HDAC7 protein, we transfected an HDAC7-FLAG fusion construct into HISM (SKN, HeLa, 10T1/2, 293, and Cos7) cells and performed indirect immunofluorescence with an anti-FLAG M2 antibody (Hendzel et al. (1998) Mol. Biol. Cell 9:2491-2507). In most cells examined, the HDAC7 protein was found predominantly in the cell nucleus. However, in a significant fraction of the transfected cells, HDAC7 was present in both the cell nucleus and cytoplasm. In some cells, HDAC7 was present in the cytoplasm only.

The relative proportion of cells containing HDAC7 expressed only in the nucleus, only in the cytoplasm, or in both the nucleus and cytoplasm varied depending on the cell line examined. For example, HDAC7 was exclusively nuclear in Cos7 cells (100% nuclear; 0% cytoplasmic only); HISM cells showed 91%, nuclear, 1.7% cytoplasmic only, and 6.8% both cytoplasmic and nuclear; SKN cells showed 93.4% nuclear HDAC7 and 0% cytoplasmic only and 6.6% nuclear and cytoplasmic; whereas only 60% of 10T1/2 cells contained HDAC7 exclusively localized in the nucleus. The relative expression levels of HDAC7 in these cell lines (10T1/2>HISM>SKN>Cos7) suggest that higher levels of expression coincide with cytoplasmic localization of HDAC7. The presence of HDAC7 in both the nucleus and cytoplasm indicates that it might shuttle in and out of the nucleus. Nucleocytoplasmic shuttling has been observed for other class II HDACs and reflects a putatively important regulatory mechanism for these factors.

Treatment of HDAC7-transfected cells with leptomycin B, a fungal toxin that inhibits CRM1-mediated nuclear export, resulted in nuclear localization of HDAC7-FLAG in most transfected cells examined. These results are in agreement with a dynamic translocation of HDAC7 in and out of the cell nucleus. In the interphase cell nucleus, HDAC7 is excluded from the nucleoli and accumulates in discrete foci devoid of DNA, as shown by DAPI staining. Such chromatin-depleted foci have been reported for other HDACs, transcription factors, and nascent mRNA species. HDAC7 was also depleted near the periphery of the cell nucleus and excluded from heterochromatic territories.

The Carboxyl-terminal Domain of HDAC7 Associates with HDAC Activity in vivo—We developed a polyclonal antiserum specific for HDAC7 by immunizing rabbits with a fusion protein between glutathione-S-transferase (GST) and the first 487 aa of HDAC7 (HDAC7 (1-487)). When tested on in vitro translated proteins, the purified antiserum recognized only HDAC7 and did not cross-react with HDAC4, 5, or 6. Western blot analysis of lysates from several cell lines showed a 105-kDa band that migrated with the same apparent molecular mass as in vitro translated HDAC7.

To test whether endogenous HDAC7 had HDAC activity, we used the anti-HDAC7 antiserum to immunoprecipitate HDAC7 from HeLa, HL60 and SupT1 cell lysates. The immunoprecipitated material was incubated with a peptide corresponding to the amino terminus of histone H4 that had been acetylated chemically and the released acetate was quantified. Specific HDAC activity was associated with the HDAC7 antiserum but not with the preimmune serum in each cell line (FIG. 3A). This activity was inhibited by trichostatin A (TSA) (400 nM), a fungal toxin that inhibits class I and II HDACs (Yoshida et al. (1999) Ann. NY Acad. Sci. 886:23-36).

Figure 3B:
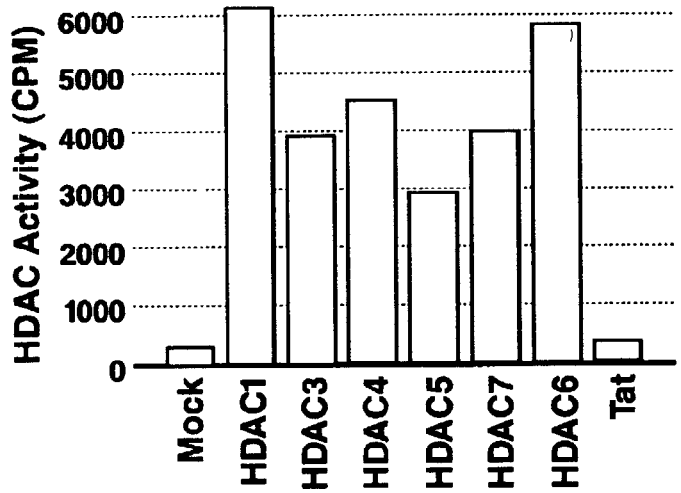

To further study the enzymatic activity of HDAC7, we transfected FLAG-tagged HDAC7 and similar constructs encoding other class I and class II HDACs into 293 cells. HDAC assays performed after anti-FLAG immunoprecipitation showed that the activity of exogenous HDAC7 is comparable to that of HDAC 1, 3, 4, 5, and 6. Western blot analysis verified that all epitope-tagged proteins were expressed and immunoprecipitated efficiently (FIG. 3B).

Figure 3C:
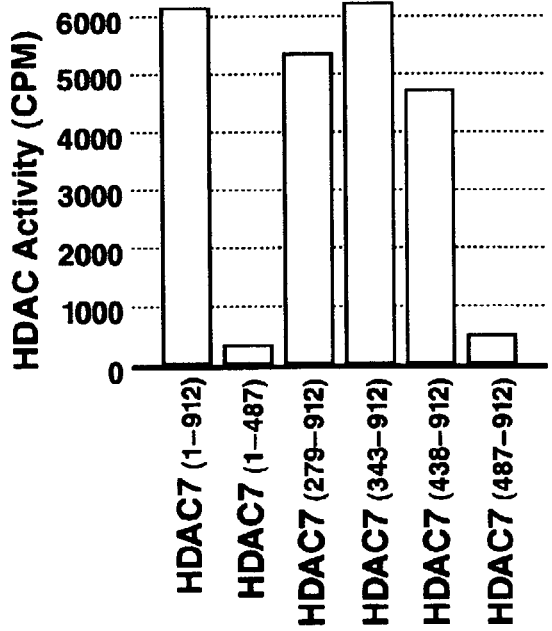
FIG. 3C depicts mapping of human HDAC7 associated HDAC activity to a carboxyl-terminal domain.

To verify that the carboxyl-terminal domain of HDAC7 is sufficient for enzymatic activity, we used a series of amino- and carboxyl-terminal deletion mutants (FIG. 3C). All deletion mutants were tagged with a carboxyl-terminal FLAG sequence and transfected into 293 cells. A domain of 478 aa corresponding to aa 438-912 of HDAC7 was necessary and sufficient for HDAC activity. Deletion of a further 49 aa at the N-terminus of this domain abolished enzymatic activity (FIG.

3C). No activity was found associated with the amino-terminal region of HDAC7. These experiments demonstrate that both endogenous and exogenous HDAC7 associate with HDAC activity in vivo and map the HDAC domain to the carboxyl-terminal region homologous to HDA1.

Enzymatic activity associated with HDAC7 is dependent on cellular factors, including HDAC3—To further analyze the enzymatic activity of HDAC7, we expressed the carboxyl-terminal fragments (aa 438-912) and (aa 487-912) as GST fusion proteins in *Escherichia coli*. No HDAC activity was detected in the recombinant protein preparations despite numerous attempts with different bacterial strains and purification protocols. The finding that the carboxyl-terminal domain of HDAC7 was associated with enzymatic activity when transfected into cells but not when expressed in bacteria suggested that HDAC7 activity requires one or more cellular cofactors.

To test this hypothesis, we bound recombinant GST-HDAC7 proteins to glutathione agarose beads and incubated them with extracts from SupT1 cells. After extensive washing, the bound material was tested for HDAC activity. GST-HDAC7 (aa 438-912) was associated with HDAC activity, while only minimal activity was associated with GST HDAC7(aa487-912), which is inactive in vivo. HDAC activity associated with GST-HDAC7 (aa438-912) was completely inhibited by TSA (400 nM). Since the class II HDACs HDAC4 and HDAC5 coimmunoprecipitate with endogenous HDAC3, we tested the material associated with GST-HDAC7 (aa487-912) for the presence of HDAC3.

Figure 4:
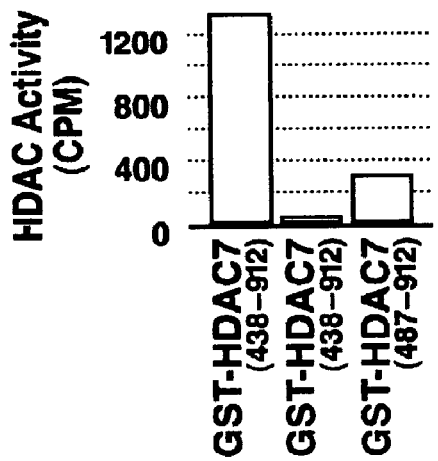
FIG. 4 depicts binding of active, but not inactive, HDAC7 to HDAC3.

Western blot analysis revealed that HDAC3 was pulled out of the extracts by the active GST-HDAC7(aa 438-912) but not the inactive GST-HDAC7(aa 487-912) (FIG. 4). This interaction was specific since neither of the highly homologous class I HDACs HDAC1 or HDAC2 did bind to GST HDAC7. Binding was not dependent on the enzymatic activity of the proteins since it was insensitive to TSA.

To confirm the interaction between HDAC7 and HDAC3 in vivo, we analyzed material immunoprecipitated with HDAC7-FLAG by western blotting. Endogenous HDAC3 coimmunoprecipitated with transfected HDAC7-FLAG but not with HDAC 1-FLAG. No association of HDAC7 with HDAC 1 or HDAC2 was detected. In contrast, HDAC 1 coimmunoprecipitated with HDAC2 as predicted by the existence of complexes containing both proteins.

HDAC7 and HDAC3 Colocalize in Discrete Structures in the Cell Nucleus—HDAC3 is an exclusively nuclear protein (Emiliani et al., supra). We predicted that if HDAC7 and HDAC3 form a functional complex in vivo, they should colocalize within the cell nucleus. The subcellular localization of HDAC7-FLAG and of endogenous HDAC3 was examined in HeLa cells using confocal fluorescence microscopy. At low expression levels of HDAC7, a micropunctuate pattern reminiscent of the nuclear patterning of endogenous HDAC1 and HDAC3 was observed. Merged images showed that HDAC7 FLAG and endogenous HDAC3 were localized in the same loci. At higher expression levels of HDAC7, larger nuclear foci were detected, similar to those observed for overexpressed HDAC4 and HDAC5. In this case, merged images showed almost complete overlap between HDAC7 FLAG and endogenous HDAC3, suggesting recruitment of endogenous HDAC3 to such focal structures.

Nuclear Localization of HDAC7 is Necessary for its HDAC Activity—The observation that HDAC7 accumulates both in the nucleus and in the cytoplasm suggested that HDAC7 could exist in two forms: in the cell nucleus complexed with HDAC3 and in the cytoplasm not associated with HDAC3. To assess the enzymatic activities of these two forms, we fractionated extracts from 293 cells transiently transfected with HDAC7-FLAG into nuclear and cytoplasmic fractions. HDAC7-FLAG was immunoprecipitated from both fractions in similar amounts. However, HDAC activity was 4.5 times higher (14762 vs. 3240 counts/min) in the nuclear fraction, where HDAC7 was associated with HDAC3. Western blot analysis of the nuclear and cytoplasmic fractions with an antiserum specific for HDAC1 (exclusively nuclear) and IKKα (exclusively cytoplasmic) showed that each fraction was around 80% pure. We conclude that only nuclear HDAC7 interacts with HDAC3 and is associated with enzymatic activity. The results are consistent with a direct involvement of HDAC3 or HDAC3 containing complexes in the enzymatic activity of HDAC7.

HDAC7 Interacts with SMRT/N-CoR In Vivo and In Vitro—To further define the role of HDAC3 in the enzymatic activity of HDAC7, we attempted to reconstitute enzymatic active complexes in vitro by using recombinant proteins. After all attempts to detect direct binding between HDAC3 and HDAC7 failed, we reasoned that additional factors might be involved in mediating the interaction. Recently, it has been reported that murine HDAC7 can directly interact with the corepressors SMRT and N-CoR (Kao et al., supra; Downes et al. (2000) *Proc. Natl. Acad. Sci. USA* 97:10330-10335). In addition, we and others found HDAC3 in multiprotein complexes containing SMRT and N-CoR.

Based on these observations we asked whether SMRT or N-CoR could be the missing link in the interaction between HDAC7 and HDAC3. Western blot analysis of material, that coimmunoprecipitated with HDAC7 under the same conditions used to analyze its enzymatic activity, indeed demonstrated binding to N-CoR and SMRT. In the same experiment material immunoprecipitated with HDAC1 contained SIN3, but not N-CoR or SMRT, demonstrating specificity of the detected interaction. Importantly, deletion analysis showed that the domain of HDAC7 corresponding to aa 438-915 that was necessary for the interaction with HDAC3, was at the same time mediating the interaction with SMRT and N-CoR.

Similar results were obtained with the GST-HDAC7 pulldown assay. These experiments indicate a strict correlation between the enzymatic activity of HDAC7 and derived constructs and their ability to simultaneously interact with HDAC3 and SMRT/N-CoR. N-CoR contains three autonomous repression domains (RD1, RD2, and RD3) that repress transcription when tethered to sequence-specific DNA-binding domains (Horlein et al. (1995) *Nature* 377:397-404; Huang et al. (2000) *Genes Dev.* 14:45-54).

Figure 5:
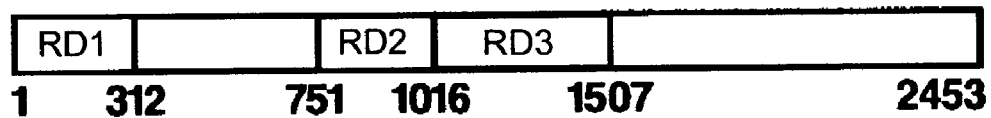
FIG. 5 depicts schematically GST fusion proteins with either RD1, RD2, or RD3.

To determine which domains of N-CoR are necessary for binding HDAC3 and HDAC7, we used GST fusion proteins with either RD1, RD2, or RD3 in pulldown experiments (FIG. 5). Full-length HDAC7 and a deletion mutant containing the active carboxyl-terminal domain (aa 438-912) bound to both GST-RD1 and GST-RD3 but not to GST-RD2. No interaction of the amino-terminal domain of HDAC7 (aa 1-487) or the inactive carboxyl-terminal fragment (aa 487-912) with RD1, RD2, or RD3 was observed. In contrast, HDAC3 was bound to GST-RD2. These results suggest that HDAC7 and HDAC3 could simultaneously bind to N-CoR by interacting with separate domains.

Figure 6A:
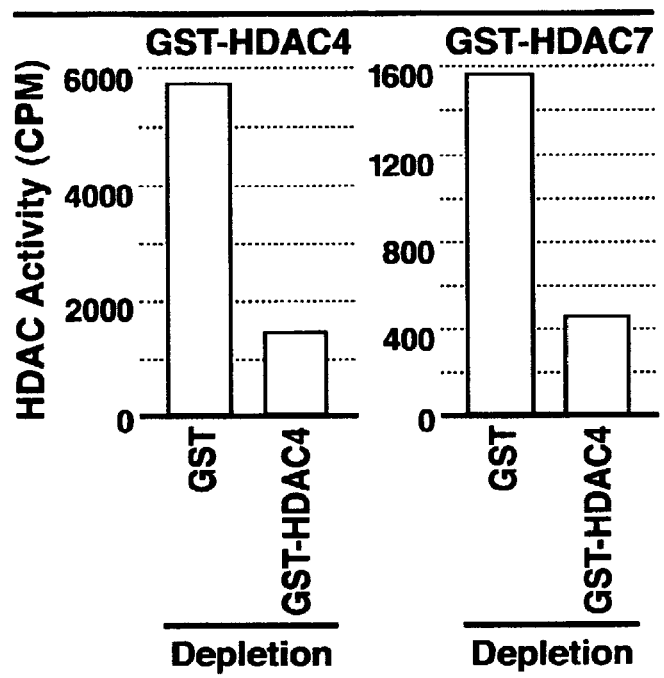
FIGS. 6A and 6B depict the role of cofactors in HDAC7 activity.

Enzymatic Activities Associated with HDAC7 and HDAC4 Are Independent but Rely on the Same Cofactors—Different members of the class II HDACs share a high degree of homology in their carboxyl-terminal domain. Since HDAC4 and HDAC5 have also been reported to bind to HDAC3 (Grozinger et al., supra), we tested whether different class II HDACs rely on the same cofactors for enzymatic activity. First, we examined the possibility that GST HDAC fusion proteins recruit common factors from cellular extracts. 293 or SupTI cellular extracts were repeatedly incubated with a recombinant fusion protein corresponding to the catalytically active domain of HDAC4 (aa 612-1084) (Fischle et al., supra) or with recombinant GST as a control. Western blot analysis demonstrated that GST-HDAC4 specifically depleted endogenous HDAC3 but not HDAC1 (FIG. 6A). Pulldown experiments using GST-HDAC4(aa 612-1084) or GST-HDAC7(aa 438-912) from the GST-HDAC4 depleted lysate showed an approximately threefold reduction in associated HDAC activity when compared with pulldowns from the GST depleted lysates (FIG. 6A). This reduction in enzymatic activity was in good agreement with the degree of HDAC3 depletion achieved (FIG. 6A). The experiment demonstrates that the enzymatic activities associated with GST-HDAC4 and GST-HDAC7 depend on common factors, including HDAC3.

Figure 6B:
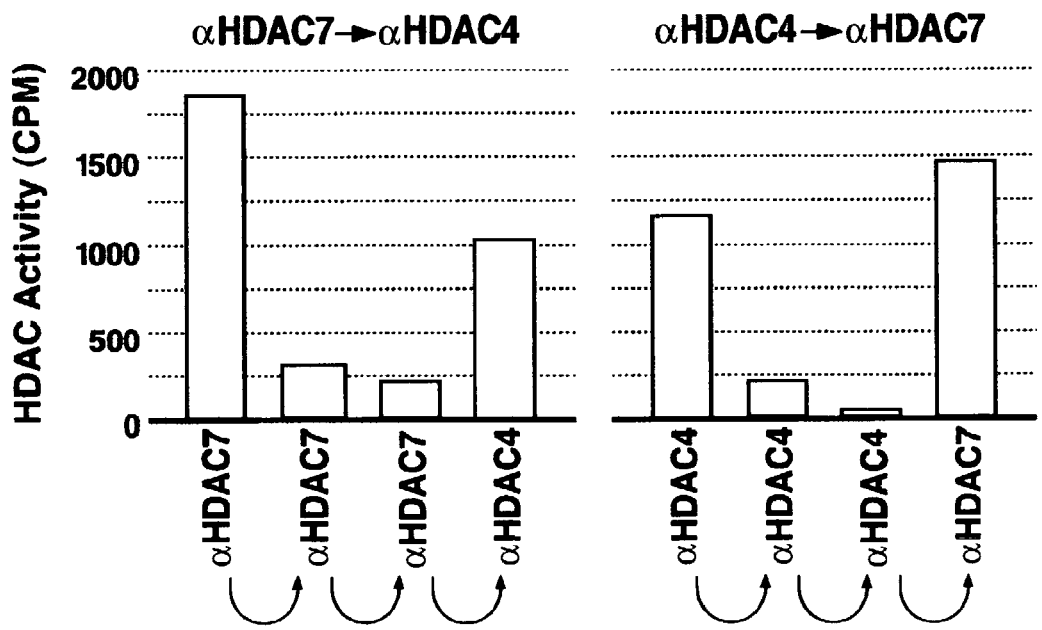

Next, we tested if stable autonomous complexes of HDAC7 and HDAC4 activity exist in vivo. Cellular extract from SupT1 cells were subjected to repeated immunoprecipitations with HDAC7-antiserum. As shown in FIG. 6A, when this HDAC7-depleted extract was immunoprecipitated with an HDAC4-specific antiserum, significant enzymatic activity was found, indicating that the enzymatic activities associated with HDAC4 and HDAC7 are present in distinct complexes in vivo. Similar results were obtained when the order of immunoprecipitations was reverted, as shown in FIG. 6B. These experiments indicate that while the enzymatic activities associated with HDAC4 and HDAC7 rely on a common set of nuclear proteins, the HDAC4 and HDAC7 proteins stably bind to their respective partners in the cell nucleus and do not readily exchange their cofactors.

Example 2

Analysis of Cell Type-Specific Expression of human HDAC7

Northern blot analysis from total human tissue RNA samples using a multi-tissue blot (Clontech) and labeled HDAC7 cDNA as a probe revealed that HDAC7 is expressed preferentially in thymus.

To investigate further the thymus-specific expression of HDAC7, quantitative reverse transcription-polymerase chain reaction (RT-PCR) analysis of purified lymphocyte populations was performed. Oligonucleotide primers that were shown to specifically amplify HDAC7 were used. Lymphocyte populations from both adult and fetal thymus were analyzed. The analyses showed that HDAC7 is expressed in $CD4^+CD8^+$ thymocytes.

These results were confirmed by histochemical analysis of thymus slices, which showed a pattern of expression consistent with expression on $CD4^+CD8^+$ thymocytes.

Example 3

A Dominant Negative Mutant of HDAC7 Induces Apoptosis in Thymocytes

Constructs encoding dominant negative mutants of HDAC7 were generated. These constructs direct expression of either the amino terminal domain (amino acids 1-437) or the carboxyl terminal domain (amino acids 438-915) of HDAC7 in mammalian cells. These construct were individually introduced into thymocytes. Apoptosis was measured using a commercially available kit. The results indicate that expression of either the amino terminal domain or the carboxyl terminal domain of HDAC7 strongly induces apoptosis in thymocytes.

To investigate this phenomenon further, we sought to determine whether levels of particular transcripts encoding transcription factors were altered when the HDAC7 fragments are expressed in thymocytes. The results indicate that mRNA encoding the transcription factor Nur77 is up-regulated when the HDAC7 fragments were expressed in thymocytes.

The above examples show that the instant invention provides the identification and characterization of a new member of the class II HDAC family, human HDAC7. In vivo, HDAC7 is associated with enzymatic activity when it is in the cell nucleus but not when it is in the cytoplasm. This enzymatic activity is dependent on the association of the carboxyl-terminal region of HDAC7 with the class I HDAC HDAC3. We provide evidence that the transcriptional corepressors SMRT and N-CoR serve as mediators that simultaneously bind class II HDACs and HDAC3 by two distinct repressor domains.

Example 4

Role of HDAC7 in Apoptosis During T Cell Selection in the Thymus

Experimental Procedures

Plasmids

The pcDNA3.1-based expression vector for C-terminal FLAG-tagged human HDAC7 has been described elsewhere. Fischle et al. (2001) *J. Biol. Chem.* 276:35826-35835. Deletion constructs of HDAC7 were generated by standard PCR and cloning procedures and have been described. Fischle et al. (2001) *J. Biol. Chem.* 276:35826-35835. Site-directed mutagenesis was performed with the Quickchange kit (Stragtagene). The identity of mutations was verified by DNA sequencing. To construct GST-fusion proteins, EcoRI fragments from the pcDNA3.1 expression constructs were subcloned into the EcoRI site of pGEX4T1 (Pharmacia), generating N-terminal GST-fusion proteins. The luciferase reporter plasmid driven by the Nur77 promoter (pNur77-Luc) was generated by cloning the -3800 to +87 genomic sequences of the Nur77 promoter into pGL2 basic (Promega). Woronicz et al. (1995) *Mol. Cell. Biol.* 15:6364-6376. Minimal MEF wild-type and mutant (RSRFwt-Luc and RSRFmut-Luc) were described elsewhere. Woronicz et al. (1995) *Mol. Cell. Biol.* 15:6364-6376.

Cell Culture, Transfections and Reporter Assay

DO11.10 T cell hybridomas were grown at 37° C., in RPMI 1640 medium supplemented with 10% FBS, 2 mM glutamine and 50U/ml of streptomycin/penicillin. Transfections were performed by the DEAE-dextran-chlororquine method. The DNA concentration was kept constant in the different samples by using the corresponding empty vector. In some cases, 16 hours after transfection cells were treated with PMA (10 ng/ml) and ionomycin (0.5 µM) for 4 hours and then harvested for reporter assay. All transfections were done in triplicate and are presented as the result of at least 3 independent experiments. Luciferase reporter assays were done with the dual luciferase reporter assay system (Promega) using an EF1α promoter-driven renilla expression vector as an internal control.

Polyclonal Cell Lines

HDAC7 constructs were cloned into HIV-1 or MSCV-based retroviral vectors. Hawley et al. (1994) *Gene Ther.* 1:136-138. These vectors allow simultaneous expression of HDAC7 and eGFP by using an internal ribosome entry site (IRES). Production of HIV-derived particles was performed as previously described. Jordan et al. (2001) *EMBO J.* 20:1726-1738. MSCV recombinant retroviruses were obtained by transfection of retroviral vector plasmids into ectopic virus packaging cells (BOSC23). Pear et al. (1993) *Proc. Natl. Acad. Sci. USA* 90:8392-8396. 0.5 $10^6$ DO11.10 cells were spin-infected for 2 hours at 2400 rpm in 200 µl of viral stock containing polybrene at 4 µg/ml (Pear et al., supra). After the spin-infection, cells were allowed to recover for 24 to 48 hours and GFP-expressing cells (approximately 30%) were sorted by flow cytometry and expended for further analysis. The percentage of GFP positive cells was stable over time and typically above 98%.

Flow Cytometry and Real-Time Polymerase Chain Reaction Analysis

Post-natal human thymus specimens were obtained from patients undergoing cardiac surgery (Moffitt Hospital at University of California San Francisco) and were processed within 6 hours of harvest. After mechanical disruption of thymus fragments, single-cell suspensions of thymocytes were stained with a mAb cocktail containing CD4-PE (Becton Dickinson), CD8-Tricolor (Becton Dickinson), and CD3-FITC (Becton Dickinson). A FACS Vantage™ (Becton Dickinson) was used to purify five thymic subsets: CD3+CD4+CD8−(SP4), CD3+CD4−CD8+(SP8), CD3+CD4+CD8+ (DP), CD3−CD4+CD8−(ITTP) and CD3−CD4−CD8−(TN). Typically, the purity of sorted cells was greater than 97%. Thymic subpopulations were frozen as dry pellets and stored at 80° C. for RNA extraction. Total RNA was extracted from frozen pellets corresponding to 105 cells by TRIZoL (Gibco-BRL) procedure following manufacturer's instructions. RNA was treated with DNaseI (RQ1 Rnase-Free Dnase, Promega) to ensure total removal of genomic DNA. Twenty µl of first-strand cDNA were generated from isolated RNA using the Gibco BRL SuperScript™ First-Strand Synthesis System for RT-PCR (Gibco BRL) following instructions. HDAC7 mRNA abundance was quantified with the TaqMan® fluorogenic detection system on an ABI Prism 7700 Sequence Detector® (Perkin-Elmer Applied Biosystems). PCR reactions were performed in duplicate with 5 µl of $1^{st}$ strand cDNA using the following primers HDAC7forward 5'-TGGTGTCTGCTGGATTTGATG-3' (SEQ ID NO:07) and HDAC7reverse 5'-ATCCAAAACATTTGGCAGAAACAT-3' (SEQ ID NO:08). FAM-5'-CCGGCCCCACTGGGTG-GCTA-3'TAMRA (SEQ ID NO:09) (Operon, Calif.) was used as a HDAC7 specific probe. PCR amplification consisted of denaturation at 95° C. for 10 min, followed by 40 cycles of denaturation at 95° C. for 15 s and annealing/extension at 58° C. for 60 s. For GAPDH detection, the TaqMan® GAPDH Control reagents Kit (Applied Biosystem, California) was used with an anneling/extension at 60° C. Standard curves were plotted for HDAC7 and GAPDH. For each sample, HDAC7 expression was standardized relatively to GAPDH.

Northern Blot Analysis

The tissue-expression of HDAC7 was analyzed as using a multiple human tissue Northern blot and RNA Master blots obtained from Clontech. Expression of Nur77 upon TSA treatment was assessed as followed. DO 11.10 cells were treated with 400 nM of TSA (Sigma) for various times. Total RNA was isolated from $10^7$ cells by the TRIZoL (GibcoBRL) procedure following manufacturer's instructions. Five µg of total RNA were used to detect the Nur77 message by standard Northern blot analysis (Sambrook, 1989). $^{32}$P-Labeled probes corresponding to human HDAC7, mouse Nur77 or human GAPDH were prepared with the Multiprime DNA labeling system (Amersham Pharmacia Biotech). Blots were prehybridized and hybridized with ExpressHyb hybridization solution (Clontech) and washed under high stringency conditions (Sambrook, 1989). Autoradiographs were analyzed with a FUJIX BAS 1000 phosphorus imaging system (Fuji, Tokyo, Japan). Quantification analysis of autoradiographs was performed on a Macintosh computer using the public domain NIH Image 1.62 program (developed at the U.S. National Institute of Health).

In situ Hybridization

The in-situ hybridization was performed according to suggested protocols (Boehringer mannheim GmbH (1996) Non-radioactive in situ hybridization application manual, $2^{nd}$ ed.). Sense and antisense digoxigenin-labeled hHDAC7 ribo-probes were prepared using the Dig RNA Labeling Kit (Boehringer mannheim) and shortened to 150-300 base long fragments by alkaline hydrolysis. Four micron thick sections of formalin-fixed paraffin-embedded tissue were deparaffinized, hydrated, pretreated with 0.2N HCl for 10 minutes and digested with proteinase K (Dako) for 25 minutes. The tissue was covered with probe solution (0.5 ng/µl) and hybridized overnight at 55° C. Excess probe was removed by stringent washes: 5×SSC for 30 minutes at 37° C., 50% formamide/50% 2×SSC for 20 minutes at 55° C., 2×SSC for 15 minutes at 42° C., 0.1×SSC for 15 minutes at 42° C. The sections were incubated with anti-digoxigenin Fab fragments conjugated with alkaline phosphatase diluted 1:300 (Boehringer mannheim) for 30 minutes, followed by the substrate BCIP/NBT (Vector Laboratories, Burlingame, Calif.) and developed overnight. The slides were washed, counterstained with nuclear fast red (Vector Laboratories).

Immunoprecipitation

Total cellular extracts from DO11.10 cells or primary thymocytes were prepared in IPLS buffer (Fischle et al. (1999) *J. Biol. Chem.* 274:11713-11720) supplemented with a protease inhibitors (Complete, Roche Molecular Biochemicals, Indianapolis) Immunoprecipitations were carried out overnight at 4° C. For FLAG-tagged proteins, M2-agarose (Sigma) antibody was used at 15 µl/ml. For immunoprecipitation of endogenous HDAC7, anti-HDAC7 antiserum was used at approximately 10 µg/ml in combination with 20µ/ml of pre-blocked (10 mg/ml of bovine serum albumin) 50% protein G-Sepharose slurry (Amersham Pharmacia Biotech). Immunoprecipitated material was washed 3 times in IPLS and 3 times in the same buffer containing 1M NaCl (Fischle et al. (1999) *J. Biol. Chem.* 274:11713-11720). Bound proteins were subjected to SDS-PAGE electrophoresis and Western blot analysis.

SDS-PAGE and Western Blotting

SDS-PAGE and Western blot analysis were performed according to standard procedures (Sambrook, 1989). Western blots were developed with the ECL detection kit (Amersham Pharmacia Biotech). Anti-HDAC7, anti-FLAG and anti-Actin antibodies were purchased from Santa Cruz Biotechnology (Santa Cruz, Calif.). Anti-mouse Nur77 and anti-MEF2D antibodies were from BD Pharmingen (San Diego, Calif.).

GST-Fusion Proteins, in vitro Translation and Pull-Downs Assays

These assays were performed as reported. Fischle et al. (2002) *Mol. Cell* 9:45-57.

Chromatin Immunoprecipitation Assays

Chromatin was prepared as described (Orlando et al., 1997) with several modifications. DO11.10 cells were activated with PMA and ionomycin. After 0, 1, 2 and 4 hours of treatment, cells were treated with 1% formaldehyde at room temperature. After 10 min, glycine was added to 0.125 M to stop the crosslinking and cells were lyzed in a buffer A (10 mM tris-HCl, pH 7.4, 10 mM NaCl, 3 mM MgCl2, 0.3 M sucrose, 10 mM Na Butyrate) containing protease inhibitors (Complete, Roche Molecular Biochemicals, Indianapolis) and 0.1% NP-40. Nuclei were pelleted in buffer A supplemented with 10 mM CaCl2 and digested with microccocal nuclease to obtain chromatin fragments with an average size of 500 base pairs. Soluble chromatin was released from nuclei by brief sonication and cleared by centrifugation. Chromatin solutions were supplemented with 0.5% sarcosyl, purified by isopicnic centrifugation on cesium chloride gradient as described (Orlando et al. (1997) *Methods* 11:205-214) stored at −70° C.

Immunoprecipitations were done overnight at 4° C. with 5 µg of an anti-acetylated Histone H3 (Upstate Biotechnology, Lake Placid, N.Y.) in immunoprecipitation buffer (IP buffer: 10 mM Tris, pH 8, 1 mM EDTA, 1% Triton X 100, 0.1% sodium deoxycholate, 0.1% SDS, 150 mM NaCl). Immune complexes were collected with protein A agarose preblocked with sonicated salmon sperm DNA and BSA (Upstate Biotechnology, Lake Placid, N.Y.). Immunoprecipitates were washed three times in washing buffer (IP buffer supplemented with 0.1 mg/ml yeast tRNA) and three times in washing buffer containing 500 mM NaCl. Finally, immune complexes were eluted in 1% SDS, 100 mM NaHCO$_3$. Formaldehyde cross-links were reverted by incubating the samples at 65° C. overnight in the presence of 200 mM NaCl. The immunoprecipitated DNA was purified by proteinase K treatment, phenol:chloroform extractions, and ethanol precipitation. Immunoprecipitated DNA and input (non-immunoprecipitated) chromatin were analyzed by PCR using the following primer pair for Nur77 promoter detection (5'-AGGGGGAGGAGATCCTGTTC-3' (SEQ ID NO:10) and 5'-ATTGACGCAGGGAGCGCGGAT-3' (SEQ ID NO:11)). Amplification products were run on a polyacrylamide gel and detected with a FUJIX BAS1000 phosphorus imaging system (Fuji, Tokyo, Japan). Quantification analysis of autoradiographs was performed on a Macintosh computer using the public domain NIH Image 1.62 program (developed at the U.S. National Institute of Health).

Results

HDAC7 Expression is Highly Enriched During DP Stage in Thymus

Figure 7:
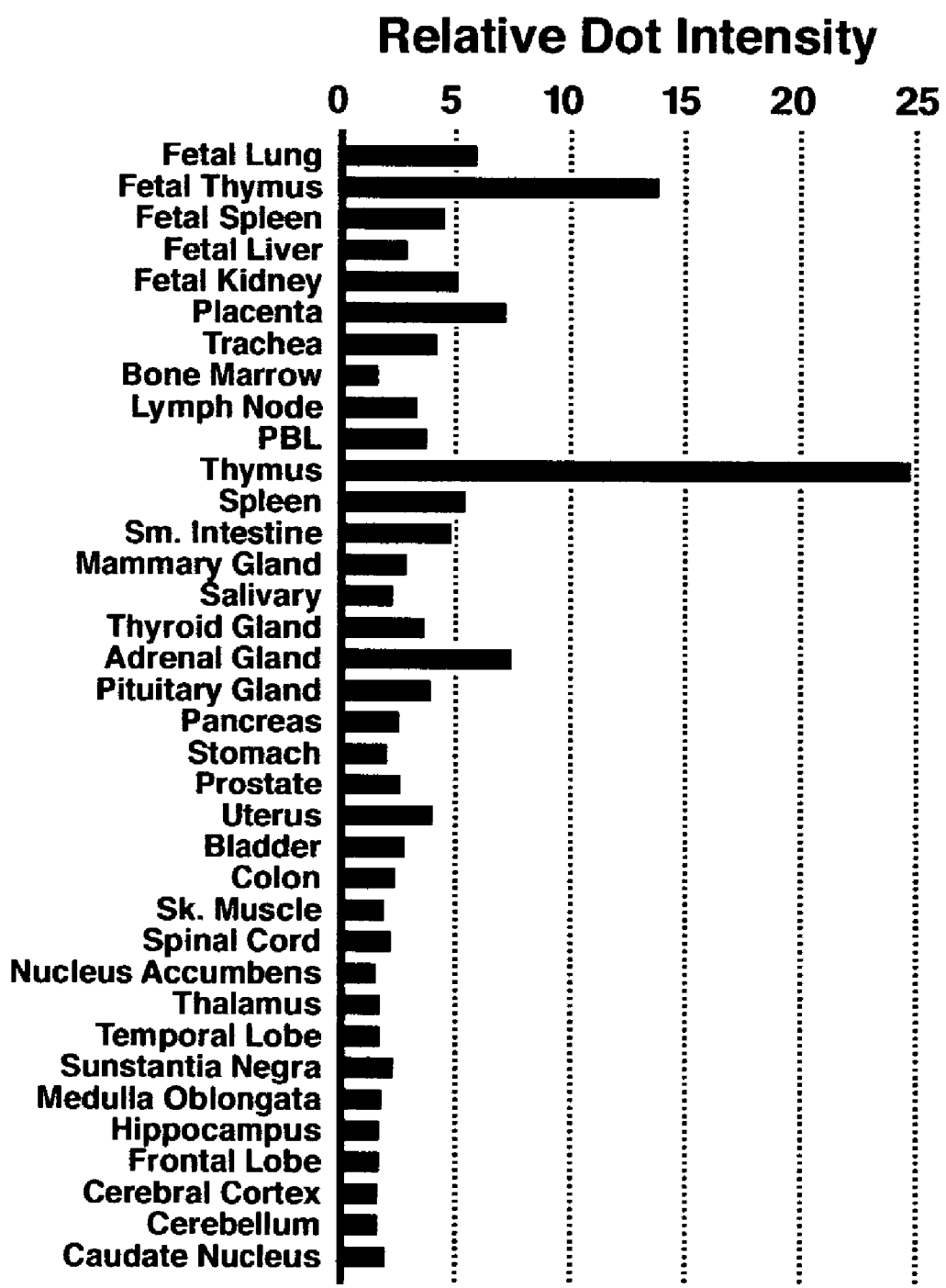
FIG. 7 depicts expression of HDAC7 mRNA in various tissues.

To establish the expression pattern of HDAC7, we performed a northern blot analysis with an hHDAC7 probe on a series of human tissues. A major transcript of 4.4 kb and a minor 6.0 kb transcript were prominently detected in human thymus. Longer exposure of the same autoradiogram showed the same transcripts in other tissues, but at significantly lower levels. Control hybridization with a GAPDH probe confirmed that similar amounts of RNA had been loaded. Using dot blot analysis, we confirmed that samples corresponding to adult and fetal thymus showed highest levels of HDAC7 mRNA (FIG. 7).

The thymus consists of an outer cortex and an inner medulla where distinct T-cell developmental events occur. To determine the precise location of HDAC7 expression within the thymus, we used in situ hybridization. Hybridization of thymic sections with an HDAC7 antisense RNA probe revealed that cells containing high levels of HDAC7 transcripts were abundant and of lymphoid morphology. These cells were located in the cortical region, where critical T-cell development events take place. No signal was obtained with the sense probe on thymic sections or with either the sense or antisense probes on spleen samples.

Figure 8:
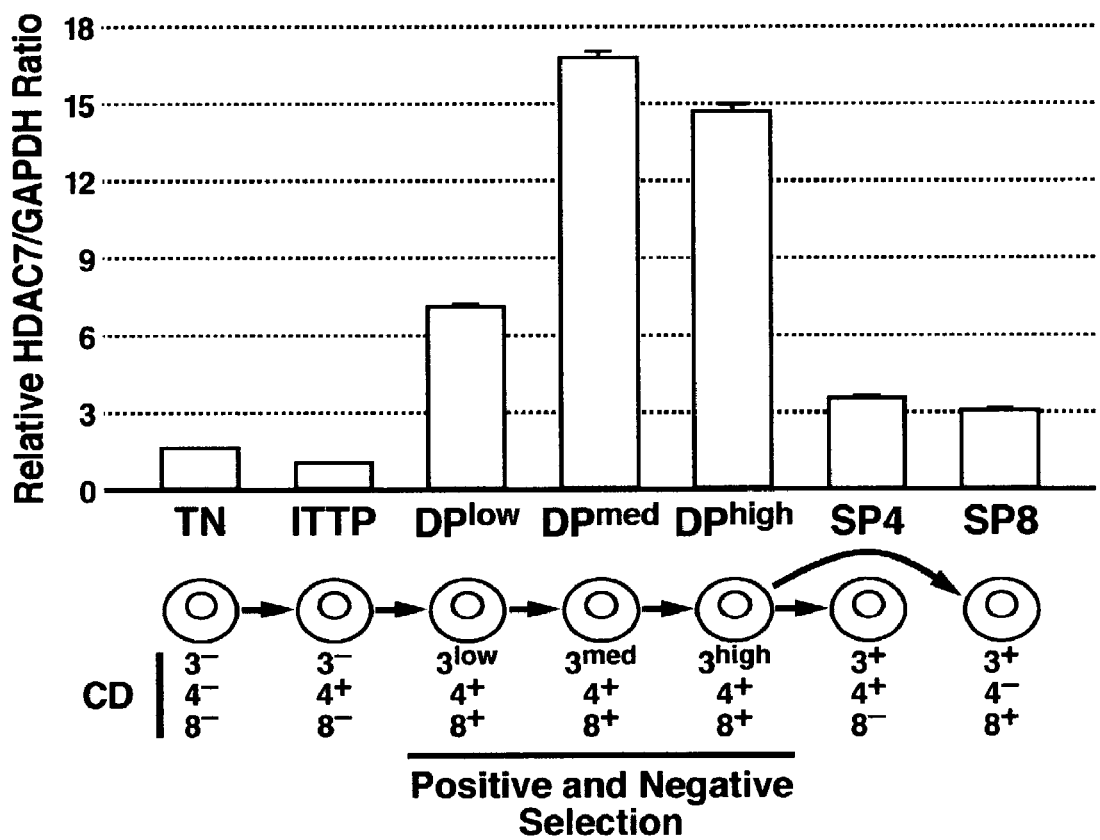
FIG. 8 depicts expression of HDAC7 during thymocyte maturation.

Within the thymus, T-cell maturation is characterized by the ordered expression of select surface markers such as CD3, CD4 and CD8. To determine the expression pattern of HDAC7 during thymocyte maturation, we sorted human primary thymocytes based on the expression of CD3, CD4 and CD8 by flow cytometry. The relative abundance of HDAC7 mRNA was assessed by real time PCR in each of these populations. Low levels of HDAC7 mRNA were observed in immature triple negative (CD3$^-$CD4$^-$CD8$^-$) thymocytes, in intrathymic T-cell precursors (CD3−CD4+, CD8−) or in mature single positive T cells (SP4 or SP8) (FIG. 8). In contrast, HDAC7 expression was highly and transiently increased during the CD4$^+$CD8$^+$ double positive (DP) stage. Within the DP thymocytes population, expression of HDAC7 was higher in the more mature CD3$^{med}$ and CD3$^{high}$ subpopulations. The DP stage represents a crucial step during T-cell development during which the peripheral T-cell repertoire is generated through positive and negative selection.

Transcriptional Activity of Nur77 is Regulated by Acetylation

The Nur77 orphan receptor has been identified as a crucial mediator of T-cell receptor (TCR)-mediated negative selection in thymocytes. Transcriptional activity of the Nur77 promoter is controlled by MEF2D, a member of the MEF2 transcription factors family. Since functional interactions have recently been identified between class II HDACs and members of the MEF2 family in muscle development, we hypothesized that HDAC7 could function as a partner for MEF2D in thymus and modulate Nur77 promoter activity during negative selection. To test this hypothesis, we first assessed the role of histone acetylation in the transcriptional activity of the Nur77 promoter. DO11.10 T-cells, a thymocyte hybridoma cell line, were treated with a histone deacetylase inhibitor, trichostatine A (TSA), and expression of Nur77 was detected by northern blot analysis. The Nur77 mRNA was not detected in untreated cells and was induced in a time dependent manner after addition of TSA to the culture medium. Similar results were obtained when levels of Nur77 protein were examined by western blot. These data suggest that the Nur77 promoter is suppressed under basal conditions via the activity of an HDAC. Such suppression could occur either directly, via the histones of the nur77 promoter, or indirectly via other factors.

To assess directly the levels of histone acetylation in the Nur77 promoter during TCR activation, we performed chromatin immunoprecipitation experiments (CHIP). Acetylated histone H3 was immunoprecipitated from cell lysates and the presence of Nur77 promoter sequences was analyzed in the immunoprecipitated material using PCR amplification of the region corresponding to the MEF2D binding sites (Youn and Liu (2000) *Immunity* 13:85-94). DO 1.10 cells were activated with a combination of PMA and ionomycin, a treatment that mimics signaling by the TCR-CD3 complex, and Nur77 protein was detected by western blot analysis. Nur77 protein levels increased in the first 2 hours after addition of PMA and ionomycin, and rapidly decrease at 4 hours. CHIP analysis revealed that the chromatin region of the Nur77 promoter encompassing the MEF2D binding sites was enriched in acetylated forms of histone H3. The relative enrichment in histone H3 acetylation closely paralleled the increase in Nur77 promoter activity and increased progressively untill 2 hours after induction and decreased back down to basal levels at 4 hour post-induction. Altogether, these data demonstrate that derepression of the Nur77 promoter by TCR activation is associated with a relative hyperacetylation of the local chromatin. These results suggest that HDAC7 could play a significant role in the repression of the Nur77 promoter.

HDAC7 Suppresses Induction of Nur77 by TCR Signaling

To determine whether HDAC7 can suppress the transcriptional activity of the endogenous Nur77 promoter, we generated polyclonal cell lines stably expressing either wild type HDAC7 or two point mutants. In agreement with our recent mutational analysis of HDAC4, another class II HDAC closely related to HDAC7 (Fischle et al., 2002), mutation H656A has no effect on the enzymatic activity of HDAC7, while mutation H657A totally abolishes its catalytic activity. DO11.10 cells were infected with a retrovirus expressing HDAC7, or its mutants, and green fluorescent protein (GFP) from a polycistronic mRNA in which the two open reading frames are separated by an internal ribosome entry site. After infection, transduced cells were sorted by flow cytometry based on GFP expression and activated by treatment with PMA and ionomycin. This treatment leads to a dramatic increase in the level of endogenous Nur77 protein in non infected cells or in cells only expressing GFP. nur77 protein induction was strongly inhibited by expression of wild type HDAC7, but not the catalytically inactive H657A mutant. As a control, the H656A mutant, which is still enzymatically active, had no effect on Nur77 protein induction.

To confirm these results, we examined the effect of HDAC7 on the transcriptional activity of the isolated Nur77 promoter driving a luciferase reporter (Woronicz et al. (1995) *Mol. Cell. Biol.* 15:6364-6376). The transfected Nur77-promoter construct was activated a hundredfold in response to PMA and ionomycin. Expression of HDAC7 inhibited Nur77 promoter activity in a dose-dependent manner. These results are consistent with the model that HDAC7 is a transcriptional repressor of Nur77.

HDAC7 Interacts with MEF2D via its Amino Terminus

Class II HDACs interact with members of the MEF2 family via a small domain located in their N-terminus. To determine whether HDAC7 interacts with MEF2D, we generated stable polyclonal cell lines expressing FLAG-tagged HDAC7 or its amino terminus. HDAC7 was immunoprecipitated with an anti-FLAG antibody and the presence of endogenous MEF2D was assessed by western blot analysis. Both full-length HDAC7 and its amino-terminus (aa 1-487) domain of HDAC7 specifically co-immunoprecipitated with endogenous MEF2D.

Next, we expressed the amino terminal (aa 1-487) and carboxy terminal (aa 438-915) regions of HDAC7 as GST fusion proteins in *Escherichia coli* and tested their ability to interact directly with in vitro translated MEF2D. In this assay, MEF2D showed a strong affinity for the amino terminal region of HDAC7, relative to its C-terminus.

To unambiguously validate the interaction between HDAC7 and MEF2D, we investigated the existence of an interaction between endogenous proteins. Total cellular extracts from T-cell hybridomas or human primary thymocytes were subjected to immunoprecipitation with an antiserum specific for HDAC7 followed by western blot analysis of the immunoprecipitated material for endogenous MEF2D. In both T-cell hybridomas and primary thymocytes, endogenous MEF2D co-immunoprecipitated with HDAC7, whereas the isotype control immunoprecipitation showed no associated MEF2D protein.

These results are consistent with the model that HDAC7 is recruited to the Nur77 promoter via interaction with MEF2D and establishes a repressive chromatin environment leading to the suppression of Nur77 transcription. To test whether HDAC7 and MEF2D remain associated or dissociate during activation of the Nur77 promoter by TCR signaling, we immunoprecipitated endogenous HDAC7 from DO11.10 cells treated or not with PMA and ionomycin. While endogenous MEF2D associated with endogenous HDAC7 in unstimulated cells, interaction of both proteins is suppressed after stimulation with PMA and ionomycin.

Interaction of HDAC7 with MEF2D is Essential for Repression of Nur77

Both HDAC4 and HDAC5 interact with MEF2 proteins via a conserved motif of 17 amino acids located in the N-terminal region of the proteins. This motif is relatively well conserved in human HDAC7 (e.g., amino acids 78-94 of SEQ ID NO:02). To determine the potential role of this motif in MEF2D binding and Nur77 repression by HDAC7, we generated mutants of HDAC7 by deleting the entire 17 amino-acid stretch or by substituting strictly conserved residues with alanine (HDAC7-K86AK88A and HDAC7-Q87AE91A). HDAC7 wild-type and mutants were synthesized and labeled in vitro and tested for their ability to interact with GST-MEF2D fusion protein in pull-down experiments. HDAC7 specifically interacted with GST-MEF2D but not with GST alone. In contrast, both the HDAC7-ΔMEF and HDAC7-K86AK88A lost their ability to interact with MEF2D while the double mutant HDAC7 Q87AE91A retained the capacity to interact with MEF2D. To confirm these observations in vivo, FLAG-tagged version of the HDAC7 mutants were transduced into DO11.10 cells. After establishment of polyclonal cell lines, stably expressed protein were immunoprecipitated using an anti-FLAG antibody and assessed for binding to endogenous MEF2D. Wild type HDAC7 and the double mutant HDAC7-Q87AE91A interacted with endogenous MEF2D while both mutants HDAC7-ΔMEF and HDAC7-K86AK88A were defective in MEF2D binding.

Figure 9:
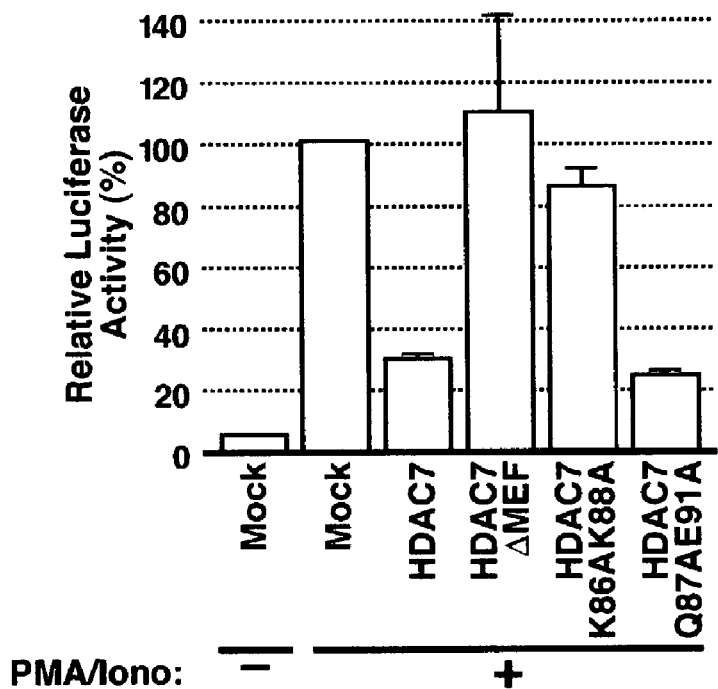
FIG. 9 depicts the effect of various HDAC7 mutants on Nur77 promoter activity.

To determine whether the MEF2D-HDAC7 interaction is essential for repression of Nur77 by HDAC7, we tested the ability of the HDAC7 mutants to repress of the Nur77 promoter following PMA and ionomycin treatment. Expression of both HDAC7 mutants unable to interact with MEF2D (HDAC7-ΔMEF and HDAC7-K86AK88A) had no effect on Nur77 promoter activity in transfection assay (FIG. 9). In contrast, the HDAC7-Q87AE91A mutant inhibited transcriptional activation of the Nur77 reporter to a degree similar to wild type HDAC7. We confirmed these results by examining the effect of the same mutants on the endogenous promoter. Polyclonal cell lines stably expressing each mutant were obtained after transduction of DO11.10 cells. As observed in transient transfection experiments HDAC7 mutants unable to interact with MEF2D (HDAC7-ΔMEF and HDAC7-K86AK88A) failed to repress the endogenous Nur77 promoter. These experiments demonstrate that the ability of HDAC7 to repress Nur77 transcription is strictly dependent on its ability to interact with MEF2D.

The Nur77 Promoter is a Specific Target for HDAC7Nter-VP16

Figure 10:
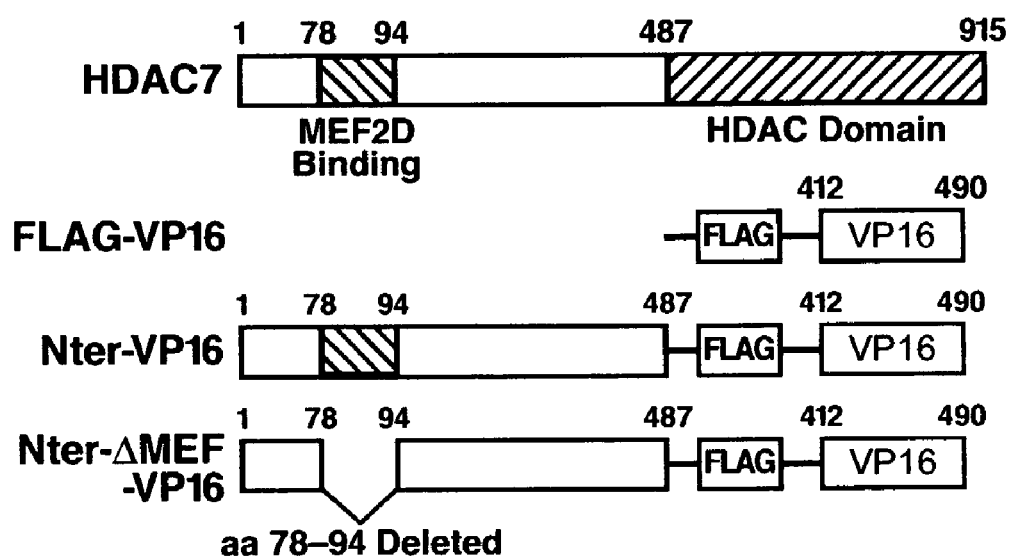
FIG. 10 depicts constructs comprising various portions of HDAC7 and VP16.

To further demonstrate the specific recruitment of HDAC7 to the Nur77 promoter, we converted HDAC7 from a transcriptional repressor to an activator by fusing its amino terminus to the herpes simplex virus VP16 transactivation domain (Nter-VP16, FIG. 10). As a control, we generated the same construct, lacking the MEF2D interaction domain (NterΔMEF-VP16). Both constructs were independently transfected in DO 11.10 cells, with pRSRFwt-Luc, a reporter construct containing four copies of the MEF2D DNA binding site from the Nur77 promoter. Cotransfection of RSRF-Luc with Nter-VP16 led to its transcriptional activation to levels similar to PMA/ionomycin activation. In contrast, the Nter-ΔMEF-VP16 protein had no effect on pRSRFwt-Luc, indicating that the MEF2D interaction with the amino terminus of HDAC7 is critical. As a control, an RSRF-Luc construct containing mutated ME2D binding sites was not affected by any of the transfected constructs, or by PMA/ionomycin treatment.

To extend these observations to the endogenous Nur77 promoter, we measured the expression of endogenous Nur77 in cells transfected with Nter-VP 16, using both northern blot analysis and a Nur77-dependent reporter (NBRE-luc). The Nur77 message was undetectable in cells transfected with the control vector, in agreement with previous published studies (Woronicz et al., 1995). Similarly NBRE-luc did not show any activity in basal conditions. In contrast, transfection of the Nter-VP16 construct but not of the NterΔMEF-VP16 led to the activation of the endogenous Nur77 expression. Similar results were obtained by measuring the activity of the NBRE-Luc construct. Finally, a NBRE-luc construct containing mutated Nur77 binding sites was not affected by any of the constructs as predicted.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated nucleic acid molecule comprising a nucleotide sequence encoding an enzymatically active histone deacetylase-7 (HDAC-7) polypeptide, wherein said HDAC-7-encoding nucleotide sequence has at least 95% nucleotide sequence identity to the coding region of SEQ ID NO:1, wherein the encoded HDAC-7 polypeptide comprises an amino acid sequence having at least 95% sequence identity to the amino acid sequence set forth in SEQ ID NO:2.

2. An expression cassette comprising a transcriptional initiation region functional in an expression host, a nucleic acid molecule encoding an enzymatically active histone deacetylase-7 (HDAC-7) polypeptide, wherein said HDAC-7-encoding nucleotide sequence has at least 95% nucleotide sequence identity to the coding region of SEQ ID NO:1, wherein the encoded HDAC-7 polypeptide comprises an amino acid sequence having at least 95% sequence identity to the amino acid sequence set forth in SEQ ID NO:2, said nucleic acid molecule under the transcriptional regulation of said transcriptional initiation region, and a transcriptional termination region functional in said expression host.

3. A genetically modified cell comprising an expression cassette according to claim 2 as part of an extrachromosomal element or integrated into the genome of a host cell as a result of introduction of said expression cassette into said host cell.

4. A method of producing a histone deacetylase, said method comprising:
   growing a cell according to claim 3, whereby said histone deacetylase is expressed; and
   isolating said histone deacetylase substantially free of other proteins.

5. The nucleic acid molecule of claim 1, wherein said HDAC-7-encoding nucleotide sequence has at least 98% nucleotide sequence identity to the coding region of SEQ ID NO:1.

6. A recombinant nucleic acid comprising a nucleotide sequence encoding an enzymatically active histone deacetylase-7 (HDAC-7) polypeptide that lacks amino terminal amino acid residues 1-437 of SEQ ID NO:2, wherein the nucleotide sequence encodes amino acids 438 to 912 of the amino acid sequence set forth in SEQ ID NO:2.

7. A recombinant nucleic acid comprising a nucleotide sequence encoding a histone deacetylase-7 (HDAC-7) polypeptide that lacks amino acids 438 to 912 of SEQ ID NO:2, wherein the nucleotide sequence encodes amino acids 1 to 437 of the amino acid sequence set forth in SEQ ID NO:2, and wherein said HDAC-7 polypeptide functions as a dominant negative mutant.

8. The expression cassette of claim 2, wherein said HDAC-7-encoding nucleotide sequence has at least 98% nucleotide sequence identity to the coding region of SEQ ID NO:1.

9. An expression cassette comprising a transcriptional initiation region functional in an expression host, a nucleic acid according to claim 7, wherein said nucleic acid is under the transcriptional regulation of said transcriptional initiation region, and a transcriptional termination region functional in said expression host.

10. An expression cassette comprising a transcriptional initiation region functional in an expression host; a nucleic acid according to claim 6, wherein said nucleic acid is under the transcriptional regulation of said transcriptional initiation region; and a transcriptional termination region functional in said expression host.

11. A genetically modified cell comprising an expression cassette according to claim 10 as part of an extrachromosomal element or integrated into the genome of a host cell as a result of introduction of said expression cassette into said host cell.

12. A genetically modified cell comprising an expression cassette according to claim 9 as part of an extrachromosomal element or integrated into the genome of a host cell as a result of introduction of said expression cassette into said host cell.

* * * * *

UNITED STATES PATENT AND TRADEMARK OFFICE
CERTIFICATE OF CORRECTION

PATENT NO. : 7,488,587 B2
APPLICATION NO. : 10/175559
DATED : February 10, 2009
INVENTOR(S) : Eric M. Verdin et al.

It is certified that error appears in the above-identified patent and that said Letters Patent is hereby corrected as shown below:

Please replace the Statement Regarding Federally Sponsored research beginning on column 1, line 13, with the following revised statement:

STATEMENT REGARDING FEDERALLY SPONSORED RESEARCH

--This invention was made with U.S. government support under grant no. GM51671 awarded by the National Institutes of Health. The United States government has certain rights in this invention.--

Signed and Sealed this

First Day of December, 2009

David J. Kappos
*Director of the United States Patent and Trademark Office*

SEQUENCE LISTING

```
<160> NUMBER OF SEQ ID NOS: 11

<210> SEQ ID NO 1
<211> LENGTH: 3889
<212> TYPE: DNA
<213> ORGANISM: Homo sapiens

<400> SEQUENCE: 1
cagcccatgg acctgcgggt gggccagcgg ccccagtgg agccccacc agagcccaca       60 ttgctggccc tgcagcgtcc ccagcgcctg caccaccacc tcttcctagc aggcctgcag     120
cagcagcgct cggtggagcc catgaggctc tccatggaca cgccgatgcc cgagttgcag    180
gtgggacccc aggaacaaga gctgcggcag cttctccaca aggacaagag caagcgaagt    240
gctgtagcca gcagcgtggt caagcagaag ctagcggagg tgattctgaa aaaacagcag    300
gcggccctag aaagaacagt ccatcccaac agccccggca ttccctacag aaccctggag    360
cccctggaga cggaaggagc cacccgctcc atgctcagca gcttttttgcc tcctgttccc    420 agcctgccca gtgaccccc agagcacttc cctctgcgca agacagtctc tgagcccaac     480
ctgaagctgc gctataagcc caagaagtcc ctggagcgga ggaagaatcc actgctccga    540
aaggagagtg cgcccccag cctccggcgg cggcccgcag agaccctcgg agactcctcc     600
ccaagtagta gcagcacgcc cgcatcaggg tgcagctccc ccaatgacag cgagcacggc    660
cccaatccca tcctgggctc ggaggctgac agtgaccgca ggacccatcc gactctgggc    720
cctcgggggc caatcctggg gagcccccac actcccctct tcctgcccca tggcttggag    780
cccgaggctg ggggcacctt gccctctcgc ctgcagccca ttctcctcct ggacccctca    840
ggctctcatg ccccgctgct gactgtgccc gggcttgggc ccttgccctt ccactttgcc    900
cagtccttaa tgaccaccga gcggctctct gggtcaggcc tccactggcc actgagccgg    960
actcgctcag agccctgcc ccagtgcc accgctcccc caccgccggg ccccatgcag       1020
ccccgcctgg agcagctcaa aactcacgtc caggtgatca agaggtcagc caagccgagt    1080
gagaagcccc ggctgcggca gataccctcg gctgaagacc tggagacaga tggcgggggga   1140 ccgggccagg tggtggacga tggcctggag cacagggagc tgggccatgg gcagcctgag    1200
gccagaggcc ccgctcctct ccagcagcac cctcaggtgt tgctctggga acagcagcga    1260
ctggctgggc ggctccccg gggcagcacc ggggacactg tgctgcttcc tctgccccag    1320
ggtgggcacc ggcctctgtc ccgggctcag tcttccccag ccgcacctgc ctcactgtca    1380
```

```
gccccagagc ctgccagcca ggcccgagtc ctctccagct cagagacccc tgccaggacc    1440
ctgcccttca ccacagggct gatctatgac tcggtcatgc tgaagcacca gtgctcctgc    1500
ggtgacaaca gcaggcaccc ggagcacgcc ggccgcatcc agagcatctg gtcccggctg    1560
caggagcggg ggctccggag ccagtgtgag tgtctccgag gccggaaggc ctccctggaa    1620
gagctgcagt cggtccactc tgagcggcac gtgctcctct acggcaccaa cccgctcagc    1680
cgcctcaaac tggacaacgg gaagctggca gggctcctgg cacagcggat gtttgtgatg    1740
ctgccctgtg gtggggttgg ggtggacact gacaccatct ggaatgagct tcattcctcc    1800
aatgcagccc gctgggccgc tggcagtgtc actgacctcg ccttcaaagt ggcttctcgt    1860
gagctaaaga atggtttcgc tgtggtgcgg ccccccaggac accatgcaga tcattcaaca    1920
gccatgggct tctgcttctt caactcagtg gccatcgcct gccggcagct gcaacagcag    1980
agcaaggcca gcaagatcct cattgtagac tgggacgtgc accatggcaa cggcacccag    2040
caaaccttct accaagaccc cagtgtgctc tacatctccc tgcatcgcca tgacgacggc    2100
aacttcttcc cggggagtgg ggctgtggat gaggtagggg ctggcagcgg tgagggcttc    2160
aatgtcaatg tggcctgggc tggaggtctg accccccca tggggatcc tgagtacctg    2220 gctgctttca ggatagtcgt gatgcccatc gcccgagagt tctctccaga cctagtcctg    2280
gtgtctgctg gatttgatgc tgctgagggt cacccgcc cactgggtgg ctaccatgtt    2340
tctgccaaat gttttggata catgacgcag caactgatga acctggcagg aggcgcagtg    2400
gtgctggcct tggagggtgg ccatgacctc acagccatct gtgacgcctc tgaggcctgt    2460
gtggctgctc ttctgggtaa cagggtggat cccctttcag aagaaggctg gaaacagaaa    2520
cccaacctca atgccatccg ctctctggag gccgtgatcc gggtgcacag taaatactgg    2580
ggctgcatgc agcgcctggc ctcctgtcca gactcctggg tgcctagagt gccaggggct    2640
gacaaagaag aagtggaggc agtgaccgca ctggcgtccc tctctgtggg catcctggct    2700
gaagataggc cctcggagca gctggtggag gaggaagaac ctatgaatct ctaaggctct    2760
ggaaccatct gcccgcccac catgcccttg gacctggtt ctcttctaac ccctggcaat    2820
agcccccatt cctgggtctt tagagatcct gtgggcaagt agttggaacc agagaacagc    2880
ctgcctgctt tgacagttat cccagggagc gtgagaaaat ccctgggtct agaatgggaa    2940
ctggagagga ccctgagagg agacgggctg ggcggcgacc cccacagggc tctcgagaac    3000
agattctccc ctccagtatg ggccctggct gtggccccca ttcctcagga ctgcacagag    3060
gaggactggc tccggctccg tcgggctcac ccttaaccac tattcctggc tctgcaaacc    3120
ccagactttg cacacagcct caggctccac acagaaatgt gaacttggcc tcagacaggc    3180
tggcccttcc taggctctag gggctagggg ggagtgggga gccaagaggt cccatattcc    3240
tgagtgcagg ggtagtccct ctcacctgct tcctcagacg actctggaag cttccctcta    3300
ccactgggca ctgagacgaa gctccctgac agccgagact ggcagccctc catctggtcc    3360
gtaccctcgc cagaggcccc cctacatcaa cctcctggcg atgccctggt ggagcagatg    3420
ggtgctctgg gagtcctgtg cttcctgatc caatggtgcc aaacccttca tctccccaag    3480
aagcgcagca taccctggg accctcggc cactgcccac tcggggagcc ttctctgttt    3540
ctggggcctc cccaccata gctctgattc ccaccccaca taggagtagc ctgactgagg    3600
gggaaggggt gggagagaag atacagacat ggaggagggg aggctgctct ggcaaagtct    3660
tcaaggcttt tggggtcca ggcctgggt caagaaggaa aatgtgtgtg agcatgtgtg    3720
tgagtgaggc gtgtgtgtga gcgtgtgtgt gagtgaggcg tgtgtgtgtg tctttcctag    3780
```

-continued

```
gacccaccat accctgtgta tgtatgcatg tttttgtaaa aaggaagaaa atggaaaaat    3840
ctgaacaata aatgttttat ttgctttaaa agcgaaaaaa aaaaaaaaa                 3889
```

<210> SEQ ID NO 2
<211> LENGTH: 915
<212> TYPE: PRT
<213> ORGANISM: Homo sapiens

<400> SEQUENCE: 2

```
Met Asp Leu Arg Val Gly Gln Arg Pro Pro Val Glu Pro Pro Pro Glu
 1               5                  10                  15

Pro Thr Leu Leu Ala Leu Gln Arg Pro Gln Arg Leu His His His Leu
            20                  25                  30

Phe Leu Ala Gly Leu Gln Gln Arg Ser Val Glu Pro Met Arg Leu
        35                  40                  45

Ser Met Asp Thr Pro Met Pro Glu Leu Gln Val Gly Pro Gln Glu Gln
 50                  55                  60

Glu Leu Arg Gln Leu Leu His Lys Asp Lys Ser Lys Arg Ser Ala Val
 65                  70                  75                  80

Ala Ser Ser Val Val Lys Gln Lys Leu Ala Glu Val Ile Leu Lys Lys
                85                  90                  95

Gln Gln Ala Ala Leu Glu Arg Thr Val His Pro Asn Ser Pro Gly Ile
            100                 105                 110

Pro Tyr Arg Thr Leu Glu Pro Leu Glu Thr Glu Gly Ala Thr Arg Ser
        115                 120                 125

Met Leu Ser Ser Phe Leu Pro Val Pro Ser Leu Pro Ser Asp Pro
 130                 135                 140

Pro Glu His Phe Pro Leu Arg Lys Thr Val Ser Glu Pro Asn Leu Lys
145                 150                 155                 160

Leu Arg Tyr Lys Pro Lys Lys Ser Leu Glu Arg Arg Lys Asn Pro Leu
                165                 170                 175

Leu Arg Lys Glu Ser Ala Pro Pro Ser Leu Arg Arg Arg Pro Ala Glu
            180                 185                 190

Thr Leu Gly Asp Ser Ser Pro Ser Ser Ser Thr Pro Ala Ser Gly
        195                 200                 205

Cys Ser Ser Pro Asn Asp Ser Glu His Gly Pro Asn Pro Ile Leu Gly
 210                 215                 220

Ser Glu Ala Asp Ser Asp Arg Arg Thr His Pro Thr Leu Gly Pro Arg
225                 230                 235                 240

Gly Pro Ile Leu Gly Ser Pro His Thr Pro Leu Phe Leu Pro His Gly
                245                 250                 255

Leu Glu Pro Glu Ala Gly Gly Thr Leu Pro Ser Arg Leu Gln Pro Ile
            260                 265                 270

Leu Leu Leu Asp Pro Ser Gly Ser His Ala Pro Leu Leu Thr Val Pro
        275                 280                 285

Gly Leu Gly Pro Leu Pro Phe His Phe Ala Gln Ser Leu Met Thr Thr
 290                 295                 300

Glu Arg Leu Ser Gly Ser Gly Leu His Trp Pro Leu Ser Arg Thr Arg
305                 310                 315                 320

Ser Glu Pro Leu Pro Pro Ser Ala Thr Ala Pro Pro Pro Gly Pro
                325                 330                 335

Met Gln Pro Arg Leu Glu Gln Leu Lys Thr His Val Gln Val Ile Lys
            340                 345                 350
```

```
Arg Ser Ala Lys Pro Ser Glu Lys Pro Arg Leu Arg Gln Ile Pro Ser
        355                 360                 365

Ala Glu Asp Leu Glu Thr Asp Gly Gly Pro Gly Gln Val Val Asp
    370                 375                 380

Asp Gly Leu Glu His Arg Glu Leu Gly His Gly Gln Pro Glu Ala Arg
385                 390                 395                 400

Gly Pro Ala Pro Leu Gln Gln His Pro Gln Val Leu Leu Trp Glu Gln
                405                 410                 415

Gln Arg Leu Ala Gly Arg Leu Pro Arg Gly Ser Thr Gly Asp Thr Val
            420                 425                 430

Leu Leu Pro Leu Ala Gln Gly His Arg Pro Leu Ser Arg Ala Gln
        435                 440                 445

Ser Ser Pro Ala Ala Pro Ala Ser Leu Ser Ala Pro Glu Pro Ala Ser
    450                 455                 460

Gln Ala Arg Val Leu Ser Ser Glu Thr Pro Ala Arg Thr Leu Pro
465                 470                 475                 480

Phe Thr Thr Gly Leu Ile Tyr Asp Ser Val Met Leu Lys His Gln Cys
                485                 490                 495

Ser Cys Gly Asp Asn Ser Arg His Pro Glu His Ala Gly Arg Ile Gln
            500                 505                 510

Ser Ile Trp Ser Arg Leu Gln Glu Arg Gly Leu Arg Ser Gln Cys Glu
        515                 520                 525

Cys Leu Arg Gly Arg Lys Ala Ser Leu Glu Glu Leu Gln Ser Val His
    530                 535                 540

Ser Glu Arg His Val Leu Leu Tyr Gly Thr Asn Pro Leu Ser Arg Leu
545                 550                 555                 560

Lys Leu Asp Asn Gly Lys Leu Ala Gly Leu Leu Ala Gln Arg Met Phe
                565                 570                 575

Val Met Leu Pro Cys Gly Gly Val Gly Val Asp Thr Asp Thr Ile Trp
            580                 585                 590

Asn Glu Leu His Ser Ser Asn Ala Ala Arg Trp Ala Ala Gly Ser Val
        595                 600                 605

Thr Asp Leu Ala Phe Lys Val Ala Ser Arg Glu Leu Lys Asn Gly Phe
    610                 615                 620

Ala Val Val Arg Pro Pro Gly His His Ala Asp His Ser Thr Ala Met
625                 630                 635                 640

Gly Phe Cys Phe Phe Asn Ser Val Ala Ile Ala Cys Arg Gln Leu Gln
                645                 650                 655

Gln Gln Ser Lys Ala Ser Lys Ile Leu Ile Val Asp Trp Asp Val His
            660                 665                 670

His Gly Asn Gly Thr Gln Gln Thr Phe Tyr Gln Asp Pro Ser Val Leu
        675                 680                 685

Tyr Ile Ser Leu His Arg His Asp Asp Gly Asn Phe Phe Pro Gly Ser
    690                 695                 700

Gly Ala Val Asp Glu Val Gly Ala Gly Ser Gly Glu Gly Phe Asn Val
705                 710                 715                 720

Asn Val Ala Trp Ala Gly Gly Leu Asp Pro Pro Met Gly Asp Pro Glu
                725                 730                 735

Tyr Leu Ala Ala Phe Arg Ile Val Val Met Pro Ile Ala Arg Glu Phe
            740                 745                 750

Ser Pro Asp Leu Val Leu Val Ser Ala Gly Phe Asp Ala Ala Glu Gly
        755                 760                 765

His Pro Ala Pro Leu Gly Gly Tyr His Val Ser Ala Lys Cys Phe Gly
```

-continued

```
                    770                 775                 780
Tyr Met Thr Gln Gln Leu Met Asn Leu Ala Gly Gly Ala Val Val Leu
785                 790                 795                 800

Ala Leu Glu Gly Gly His Asp Leu Thr Ala Ile Cys Asp Ala Ser Glu
                805                 810                 815

Ala Cys Val Ala Ala Leu Leu Gly Asn Arg Val Asp Pro Leu Ser Glu
            820                 825                 830

Glu Gly Trp Lys Gln Lys Pro Asn Leu Asn Ala Ile Arg Ser Leu Glu
        835                 840                 845

Ala Val Ile Arg Val His Ser Lys Tyr Trp Gly Cys Met Gln Arg Leu
850                 855                 860

Ala Ser Cys Pro Asp Ser Trp Val Pro Arg Val Pro Gly Ala Asp Lys
865                 870                 875                 880

Glu Glu Val Glu Ala Val Thr Ala Leu Ala Ser Leu Ser Val Gly Ile
                885                 890                 895

Leu Ala Glu Asp Arg Pro Ser Glu Gln Leu Val Glu Glu Glu Pro
            900                 905                 910

Met Asn Leu
        915

<210> SEQ ID NO 3
<211> LENGTH: 29
<212> TYPE: DNA
<213> ORGANISM: Artificial Sequence
<220> FEATURE:
<223> OTHER INFORMATION: synthetic primer

<400> SEQUENCE: 3
cggaattcca gcccatggac ctgcgggtg                                    29

<210> SEQ ID NO 4
<211> LENGTH: 28
<212> TYPE: DNA
<213> ORGANISM: Artificial Sequence
<220> FEATURE:
<223> OTHER INFORMATION: synthetic primer

<400> SEQUENCE: 4
cggaattcga ccgagtcata gatcagcc                                     28

<210> SEQ ID NO 5
<211> LENGTH: 34
<212> TYPE: DNA
<213> ORGANISM: Artificial Sequence
<220> FEATURE:
<223> OTHER INFORMATION: synthetic primer

<400> SEQUENCE: 5
cggaattcac catggccccg ctgctgactg tgcc                              34

<210> SEQ ID NO 6
<211> LENGTH: 29
<212> TYPE: DNA
<213> ORGANISM: Artificial Sequence
<220> FEATURE:
<223> OTHER INFORMATION: synthetic primer

<400> SEQUENCE: 6
cggaattcga gattcatagg ttcttcctc                                    29

<210> SEQ ID NO 7
```

```
<211> LENGTH: 21
<212> TYPE: DNA
<213> ORGANISM: Artificial Sequence
<220> FEATURE:
<223> OTHER INFORMATION: synthetic primer

<400> SEQUENCE: 7
tggtgtctgc tggatttgat g                                            21

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
atccaaaaca tttggcagaa acat                                         24

<210> SEQ ID NO 9
<211> LENGTH: 20
<212> TYPE: DNA
<213> ORGANISM: Artificial Sequence
<220> FEATURE:
<223> OTHER INFORMATION: synthetic probe

<400> SEQUENCE: 9
ccggccccac tgggtggcta                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10 aggggagga gatcctgttc                                               20

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
attgacgcag ggagcgcgga t                                            21
```